(12) United States Patent
Yasukohchi et al.

(10) Patent No.: US 6,455,639 B1
(45) Date of Patent: *Sep. 24, 2002

(54) OXIRANE DERIVATIVE AND PROCESS FOR THE PREPARATION THEREOF

(75) Inventors: Tohru Yasukohchi; Kouzoh Sanchika; Chika Itoh; Kei-ichi Maruyama, all of Kanagawa (JP)

(73) Assignee: NOF Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/367,642

(22) PCT Filed: Mar. 23, 1999

(86) PCT No.: PCT/JP99/01451

§ 371 (c)(1),
(2), (4) Date: Aug. 19, 1999

(87) PCT Pub. No.: WO99/48948

PCT Pub. Date: Sep. 30, 1999

(30) Foreign Application Priority Data

Mar. 24, 1998 (JP) .......................................... 10-076286

(51) Int. Cl.[7] .............................................. C08G 65/28
(52) U.S. Cl. ....................... 525/408; 525/409; 528/405; 528/421; 568/618; 568/621; 568/622
(58) Field of Search ................................ 528/405, 421; 525/408, 409; 568/618, 621, 622

(56) References Cited

U.S. PATENT DOCUMENTS 3,293,193 A 12/1966 Krahler et al.
4,721,816 A 1/1988 Edwards
4,967,016 A * 10/1990 Kemp
5,605,976 A * 2/1997 Martinez

FOREIGN PATENT DOCUMENTS

| EP | 0 826 715 | | 3/1998 |
|---|---|---|---|
| JP | 58-185622 | | 10/1953 |
| JP | 53-119809 | | 10/1978 |
| JP | 1-149752 | | 6/1989 |
| JP | 4-214722 | | 8/1992 |
| JP | 8165343 | * | 6/1996 |
| JP | 10-53647 | | 2/1998 |
| JP | 10-168177 | | 6/1998 |
| JP | 8-268919 | | 10/1998 |

OTHER PUBLICATIONS

International Search Report.

European Search Report for EP 99 90 9309 dated Sep. 3, 2001.

Harris, J., "Laboratory Synthesis of Polyethylene Glycol Derivatives," *Journal of Macromolecular Science–Reviews in Macromolecular Chemistry*, pp. 325–373 (1985).

Database WPI, Derwent Publications, Ltd., XP 002174922, Jun. 25, 1996.

* cited by examiner

*Primary Examiner*—David J. Buttner
(74) *Attorney, Agent, or Firm*—Sughrue Mion, PLLC

(57) ABSTRACT

An oxirane derivative and process for preparation of the same, having a high purity characterized in terms of gel permeation chromatography and thin layer chromatography. The oxirane derivative is useful as a starting material for medical purposes, and mainly drug delivery systems.

42 Claims, 16 Drawing Sheets

OXIRANE DERIVATIVE AND PROCESS FOR THE PREPARATION THEREOF

TECHNICAL FIELD

The present invention relates to an oxirane derivative and a process for the preparation thereof. More particularly, the present invention relates to a high molecular oxirane derivative having a narrow molecular weight distribution, little impurity content and a high purity useful as a starting material of terminal-modified oxirane derivative for medical purposes, particularly for chemical modification of physiologically active protein such as polypeptide and enzyme and chemical modification in drug delivery system for liposome, polymer micelle, etc., and a process for the preparation thereof.

BACKGROUND ART

In recent years, terminal-modified oxirane compounds have attracted attention as an important carrier for drug delivery system. Thus, compounds having amino group or carboxyl group incorporated in oxirane compound have been under extensive study. As such terminal-modified oxirane compounds there have been exemplified 2,4-bis (methoxypolyethylene glycol)-6-chloro-s-triazine containing triazine ring as inclusion (JP-A-3-72469 (The term "JP-A" as used herein means an "unexamined published Japanese patent application")), and compound obtained by converting terminal hydroxyl group in methoxypolyethylene glycol to carboxymethyl group, and then converting it to hydroxysuccinimide ester (E. Dellacherie et al., "Macromol. Chem. Suppl.", 9, pp.43–46, 1985). Examples of publications carrying these terminal-modified oxirane compounds and their application include J. Milton Harris, "Laboratory Synthesis of Polyethylene Glycol Derivatives", Macromol. Chem. Phys., C25 (3), pp.325–375, 1985, K. Takahashi, A. Ajima, et al, "Biochemical and Biophysical Research Commu.", Vol. 125, No. 2, pp. 761–766, 1984, Y. Kamisaki, H. Wada, et al., "The Journal of Pharmacology and Experimental Therapeutics",Vol. 216, No.2, pp.410–414, 1981, Y.Kamisaki, H. Wada, et al., "Gann", Vol. 73, pp. 470–474, 1982; A. Matsushima, H. Nishimura, et al., "Chemistry Letters", pp. 773–776, 1980, K. Ono, Y. Kai, H. Maeda et al., "J. Biomater. Sci. Polymer Edn.",Vol. 2, No. 1, pp.61–65, 1991, and T. Yoshimoto, H. Nishimura, Y. Saito, et al., "Jpn. J. Cancer Res. (Gann)", Vol. 77, pp. 1,264–1,270, 1986. Such a terminal-modified oxirane compound can be prepared by subjecting as a starting material a high molecular compound obtained by adding oxirane or alkyloxirane to a compound containing active hydrogen to reaction on the terminal hydroxyl group so that it is converted to a compound having various functional groups. Known examples of the oxirane compound to be used as a starting material include a compound having one hydroxyl group obtained by adding oxirane or alkyloxirane to aliphatic or aromatic alcohol, and a compound having two or more hydroxyl groups obtained by adding alkyloxirane to polyhydric alcohol.

On the other hand, these terminal-modified high molecular oxirane compounds are mostly used for medical purposes and need to be high purity compounds. Thus, various proposals have been made for such high purity compounds and their preparation processes. For example, JP-A-3-72469 and JP-A-8-165343 refer to percent modification of terminal hydroxyl group in oxirane compound and propose a synthesis method little liable to production of by-products which comprises removing impurities produced as much as possible at the purification step to prepare a high purity terminal-modified oxirane compound. The preparation method proposed places emphasis of interest on the purification during the preparation of terminal-modified derivative from oxirane derivative but takes into little account impurities contained in the oxirane compound to be used as a starting material. As a result, terminal-modified compounds derived from oxirane similar compounds having different molecular weights or different numbers of functional groups can be hardly removed depending on their structure because their physical properties are very similar to that of the desired compound. Even if these terminal-modified compounds can be removed anyway, many steps are required. Further, yield drop or other problems occur.

For example, when it is attempted to synthesize a terminal-modified oxirane compound from as a starting material an oxirane compound having one hydroxyl group such as methoxypolyethylene glycol, a terminal-modified oxirane compound having a predetermined molecular weight which is modified for only one hydroxyl group is designed pharmaceutically. Thus, if the resulting compound contains a terminal-modified compound having two hydroxyl groups as an impurity or compounds having different molecular weights, no desired compound can be obtained, causing a great problem in the design of quality of drug. For example, if a large amount of by-products are produced, it is necessary to examine the by-products for toxicity, occasionally giving a necessity of effecting experiment and clinically study again.

In general, an oxirane compound having one hydroxyl group can be obtained by subjecting a monohydric alcohol having one hydroxyl group as a starting material to addition reaction with oxirane in the presence of an alkaline catalyst such as potassium hydroxide and sodium hydroxide or a Lewis acid catalyst such as boron trifluoride and tin tetrachloride. If water molecules contained in the catalyst or alcohol as a starting material are present in the reaction system, oxirane is added to the water molecules to produce a polyethylene glycol having two hydroxyl groups. The polyethylene glycol has two reaction points and thus has oxirane added thereto in an amount of about twice that of the desired compound having one reaction point and hence a molecular weight as much as about twice that of the desired compound.

If the alcohol to be used as a starting material has a large number of carbon atoms and hence a boiling point of remarkably higher than that of water, the removal of water content from the system by dehydration of the reaction system having the catalyst charged therein under reduced pressure makes it possible to reduce somewhat the produced amount of diol compound as a by-product. On the contrary, however, if the alcohol to be used as a starting material has a small number of carbon atoms and hence a boiling point close to or lower than that of water, water content cannot be removed from the reaction system by dehydration under reduced pressure. In most cases, however, as alcohol to be used as a starting material from which a terminal-modified high molecular oxirane compound to be used as a starting material of drug is prepared there are used $C_{1-4}$ aliphatic alcohol or $C_{6-7}$ aromatic alcohol which are used as a protective group for hydroxyl group.

It has been suggested that decomposition reaction can occur as well depending on the reaction temperature and amount of catalyst to produce a low molecular vinyl compound (Yoshihiko Oshima et al., "Coating Engineering", Vol. 22, No. 9, pp. 397–403, 1987). Such a vinylether can be easily hydrolyzed under acidic conditions to produce a hydroxyl group. Thus, if a mineral acid or the like is used to remove the alkaline catalyst, such a vinylether becomes an oxirane derivative having a different molecular weight from that of the main component which then becomes a terminal-modified compound having a different molecular weight from the desired compound at the subsequent reaction. On the other hand, if no mineral acid is used to remove the catalyst, the vinylether remains to be a vinyl group which then is left unreacted at the step of introducing a functional group into the terminal of polyoxirane derivatives. Thus, the vinylether remains as an impurity. Further, it is known that the polymerization of cyclic monomers such as oxirane involves monomer addition reaction which is not accompanied by chain end and the resulting polymer has a Poisson distribution (P. J. Flowrie, "High Molecular Chemistry", 2nd vol., pp. 314–315, translated by Shoten Oka, Maruzen, 1964). It is also known that the ratio of weight-average molecular weight Mw to number-average molecular weight Mn is represented by the following equation, supposing that the number of moles of oxirane added to the starting material is a:

$$Mw/Mn = 1 + a/(a+1)^2$$

The closer the polydispersion degree calculated from the foregoing equation and the polydispersion degree measured are to each other, the more uniform is the resulting polymer. However, it is also known that as the molecular weight of the polymer increases, the actual polydispersion degree and the value calculated from Poisson distribution equation deviate from each other (Yoshihiko Oshima et al., "Coating Engineering", vol. 22, No. 9, pp. 397–403, 1987). This means that many oxirane derivatives cannot be obtained by uniform reaction.

If a terminal-modified oxirane compound is synthesized from an oxirane compound containing impurities, various impurities are newly produced. Since these impurities have physical properties similar to that of the desired compound, they can be hardly removed effectively. Further, if the terminal-modified oxirane compound is bonded to drug while containing these impurities, the resulting drug is heterogeneous, making it extremely difficult to invariably provide drug with constant quality. Therefore, the oxirane compound to be used as a starting material of terminal-modified oxirane compound needs to be a high purity oxirane compound free of these impurities. If the oxirane compound has a low molecular weight, these impurities can be removed by any purification method such as distillation. However, if the desired compound has a high molecular weight, a high purity and high molecular alkoxypolyoxysirane derivatives cannot be efficiently obtained as desired compound from the oxirane compound containing these impurities depending on some industrial separation/purification processes, e.g., recrystallization, reprecipitation, ultrafiltration, fractional liquid chromatography. Thus, no high purity and high molecular oxirane compounds free of high molecular and low molecular impurities and having a polydispersion degree showing good approximation to Poisson distribution equation have ever been obtained.

The present invention has been worked out for the purpose of providing a high molecular oxirane derivative having a narrow molecular weight distribution, little impurity content and a high purity useful as a starting material of terminal-modified oxirane derivative for medical purposes, particularly for chemical modification of physiologically active protein such as polypeptide and enzyme and chemical modification in drug delivery system like liposome, polymer micelle, etc., and a process for the preparation thereof.

DISCLOSURE OF THE INVENTION

The inventors made extensive studies of solution to the foregoing problems. As a starting material, an oxirane derivative, particularly one having one hydroxyl group, was studied. As a result, it was found that most oxirane derivatives contain a compound having a molecular weight as much as about twice that of the desired compound and a low molecular compound in a large amount. It was also found that the compound as main component has a distribution drastically deviating from Poisson distribution and thus is not homogeneous. A further study was made on these oxirane derivatives. As a result, analysis by thin layer chromatography shows that these oxirane derivatives each exhibit two or three spots having different Rf values. This is because gel permeation chromatography involves a system for separation by molecular weight and thus can hardly perform separation of impurities having a molecular weight equal or similar to the main component, if any, while thin layer chromatography is a system for separation by polarity of compound and thus can perform separation of compounds which cannot be separated by gel permeation chromatography. A still further study was made on the basis of this knowledge. As a result, an oxirane derivative which exhibits a high purity as analyzed not only by gel permeation chromatography but also by thin layer chromatography and a process for the preparation thereof were successfully developed.

The present invention provides the following compounds and preparation processes:

(1) An oxirane derivative represented by the following general formula [1]:

$$RO(C_2H_4O)nH \qquad [1]$$

wherein R represents a $C_{1-7}$ hydrocarbon group; and n represents the average number of moles of oxirane groups added, ranging from 20 to 900, characterized in that the following requirements are satisfied:

(A) Supposing that the straight line between the elution tarting point and the elution end point on chromatogram obtained by gel permeation chromatography is PbaseL, the total peak area above PbaseL is Parea, the height of the top Ptop of the maximum peak of refractive index from PbaseL is PtopH, and the peak area between the point at which the height of the elution curve from the elution starting point toward Ptop from PbaseL is ⅕ of PtopH and the point at which the height of the elution curve from Ptop toward the elution end point is ⅕ of PtopH is PareaM, Parea and PareaM satisfy the following relationship:

$$PareaM/Parea \geq 0.85;$$

and (B) When thin layer chromatography is effected by development with a 85:15 (by volume) mixture of chloroform and methanol, followed by color development with iodine and measurement of the purity of various spots by a densitometer, main spots having Rf value falling within the range of from 0.2 to 0.8 have a purity of not less than 98%.

(2) The oxirane derivative as defined in Clause (1) wherein Parea and PareaH satisfy the following relationship:

$$PareaH/Parea \leq 0.05$$

where PareaH is the peak area between the elution starting point on chromatogram and the point at which the height of the elution curve toward Ptop from PbaseL is ⅕ of PtopH.

(3) The oxirane derivative as defined in Clause (1) or (2), wherein the number of moles of oxirane added PtopEOmol determined by the following equation:

$$PtopEOmol=(PtopMw-ROHMw)/44$$

supposing that the molecular weight corresponding to the top of the peak on chromatogram is PtopMw and the molecular weight of the compound ROH (in which R represents a $C_{1-7}$ hydrocarbon group) to be used as a starting material is ROHMW, satisfies the following relationship with the ratio PMmw/mn of weight-average molecular weight to number-average molecular weight of the region represented by PareaM determined by gel permeation chromatography:

$$PMmw/mn-[1+PtopEOmol/(1+PtopEOmol)^2]\leq 0.02$$

(4) The oxirane derivative as defined in any one of Clauses (1) to (3), wherein R in the general formula [1] is $CH_3$.

(5) A process for the preparation of an oxirane derivative defined in any one of Clauses (1) to (3), characterized in that the water content in the reaction system where the compound ROH (in which R represents a $C_{1-7}$ hydrocarbon group) and oxirane react with each other is not more than 5 ppm.

(6) The process for the preparation of an oxirane derivative as defined in Clause (5), wherein R in the general formula [1] is $CH_3$.

(7) An oxirane derivative represented by the following general formula [2] prepared from an oxirane derivative as defined in any one of Clauses (1) to (4) as a starting material:

$$RO(C_2H_4O)n-Xp-Y \qquad [2]$$

wherein R represents a $C_{1-7}$ hydrocarbon group; n represents an integer of from 20 to 900; X represents a $C_{1-3}$ hydrocarbon group or —$CO(CH_2)q$— (in which q is an integer of from 2 to 4); Y represents an amino group or carboxyl group; and p represents 0 or 1.

BEST EMBODIMENTS OF IMPLICATION OF THE INVENTION

An embodiment of the oxirane derivative of the present invention has a structure represented by the following general formula [1]:

$$RO(C_2H_4O)nH \qquad [1]$$

In the foregoing general formula [1], R represents a $C_{1-7}$ hydrocarbon group. n represents the average number of moles of oxirane group added which ranges from 20 to 900. Examples of the $C_{1-7}$ represented by R include $C_{1-7}$ alkyl groups such as methyl, ethyl, propyl, isopropyl, butyl, isobutyl, sec-butyl, t-butyl, pentyl, isopentyl, hexyl, isohexyl, heptyl and isoheptyl, phenyl group, and benzyl group. If the number of carbon atoms contained in the hydrocarbon group represented by R is not less than 8, the oxirane derivative represented by the general formula [1] exhibits a raised surface activity, possibly giving adverse effects on the solubility of medical terminal-modified compound. Preferred among these hydrocarbon groups are methyl group, ethyl group, and benzyl group. Particularly preferred among these hydrocarbon groups are methyl group and benzyl group.

n representing the number of moles of oxirane added is from 20 to 900, preferably from 50 to 900, more preferably from 100 to 900. If n falls below 20, the resulting oxirane derivative insufficiently improves the function of the drug to be bonded thereto. Further, the resulting oxirane derivative can possibly exerta stronger effect on cells. On the contrary, if f exceeds 900, the resulting oxirane derivative can exhibit a remarkably deteriorated handleability.

In the oxirane derivative of the present invention having a structure represented by the general formula [1], supposing that the straight line between the elution starting point and the elution end point on chromatogram obtained by gel permeation chromatography is PbaseL, the total peak area above PbaseL is Parea, the height of the top of the maximum peak of refractive index: Ptop, with respect to PbaseL is PtopH, and the peak area between the point at which the height of the elution curve from the elution starting point toward Ptop, with respect to PbaseL is ⅕ of PtopH and the point at which the height of the elution curve from Ptop toward the elution end point, with respect to PbaseL is ⅕ of PtopH is PareaM, Parea and PareaM satisfy the following relationship:

$$PareaM/Parea \geq 0.85$$

However, the foregoing relationship takes into account only the peak arising from the oxirane derivative, excluding the peak attributed to the developing solvent used in gel permeation chromatography or the pseudo-peak attributed to the fluctuations of base line attributed to the column or apparatus used.

Figure 1:
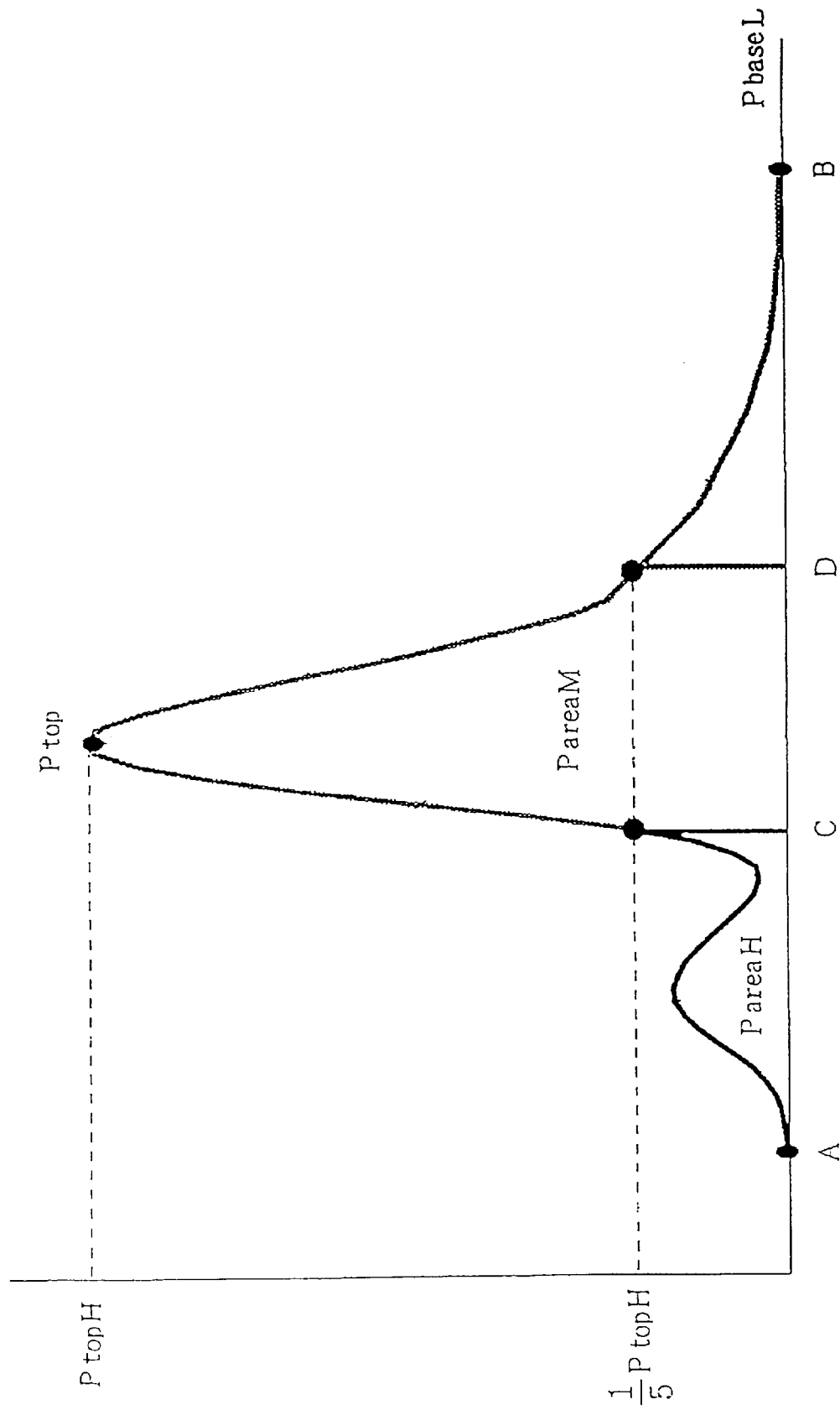
FIG. 1 is a model chart illustrating chromatogram obtained by gel permeation chromatography of an oxirane derivative.

FIG. 1 is a model chart illustrating chromatogram obtained by gel permeation chromatography of an oxirane derivative. When the specimen solution is injected into the gel permeation chromatograph where it is then developed, a component having the highest molecular weight begins to be eluted at the elution starting point A. Inmost cases, a portion having a relatively high molecular weight shows a small peak, followed by the fall of the elution curve. Subsequently, the elution of main component causes the formation of main peaks including the maximum refractive index peak. Thereafter, the elution curve gradually falls to the elution end point B where a component having the lowest molecular weight is eluted to terminate development. The straight line between the elution starting point and the elution end point is defined as PbaseL. The total peak area above PbaseL is defined as Parea. The peak area between the point C at which the height of the elution curve from the elution starting point toward Ptop from PbaseL is ⅕ of PtopH and the point D at which the height of the elution curve from Ptop toward the elution end point is ⅕ of PtopH is defined as PareaM. The peak area between the elution starting point A and the point C at which the height of the elution curve from the elution starting point toward Ptop from PbaseL is ⅕ of PtopH is defined as PareaH.

The oxirane derivative of the present invention has PareaM/Parea of not less than 0.85, preferably not less than 0.88, more preferably not less than 0.91. The greater PareaM/Parea is, the narrower is the molecular weight distribution of oxirane derivative and hence the less is the content of high molecular or low molecular impurities. If PareaM/Parea falls below 0.85, the molecular weight distribution is wider, increasing the content of high molecular or low molecular impurities and hence possibly giving an insufficient purity of starting material for medical purposes.

The oxirane derivative of the present invention has PareaH/Parea of not more than 0.05, preferably not more than 0.04, more preferably not more than 0.03. The smaller PareaH/Parea is, the less is the content of high molecular impurities. If PareaH/Parea exceeds 0.05, the resulting oxirane derivative has an increased content of high molecular impurities and thus, when used as a starting material for medical purposes, can produce by-products, whereby the purity of the desired drug is lowered.

For gel permeation chromatography herein, SHODEX GPC SYSTEM-11 is used as GPC system, SHODEX RI-71 is used as a differential refractometer and three columns of SHODEX KF804L ($\phi$8 mm×300 mm) connected in series are used as a GPC column. Tetrahydrofuran is allowed to flow at a rate of 1 ml/min as a developing solvent at a column oven temperature of 40° C. Under these conditions, 0.1 ml of a 0.1 wt-% specimen solution is then injected into the column. Various measurements can be obtained by subjecting the elution curve to analysis by BORWIN GPC calculation program.

When subjected to thin layer chromatography by development with a 85:15 (by volume) mixture of chloroform and methanol, followed by color development with iodine and measurement of the purity of various spots by a densitometer, the oxirane derivative of the present invention shows a purity of not less than 99%, preferably not less than 98% in main spots having Rf value falling within the range of from 0.2 to 0.8. When main spots separated by thin layer chromatography have a high purity, it means that the oxirane derivative is homogeneous from the standpoint of polarity and molecular weight. If the purity of main spots falls below 98%, the resulting oxirane derivative can have an insufficient purity as a starting material for medical purposes.

As the thin layer plate to be used in thin layer chromatography herein there may be used, e.g., a laminate of silica gel 60 glass (Merck Japan Ltd.; 3 cm×12 cm). As the developing solvent there is used a 85:15 mixture (by volume) of chloroform and methanol. The amount of the specimen to be spotted on the thin layer plate is preferably from 30 to 200 $\mu$g, more preferably from 50 to 100 $\mu$g. The developing distance needs to be not less than 5 cm, preferably not less than 8 cm.

Figure 2:
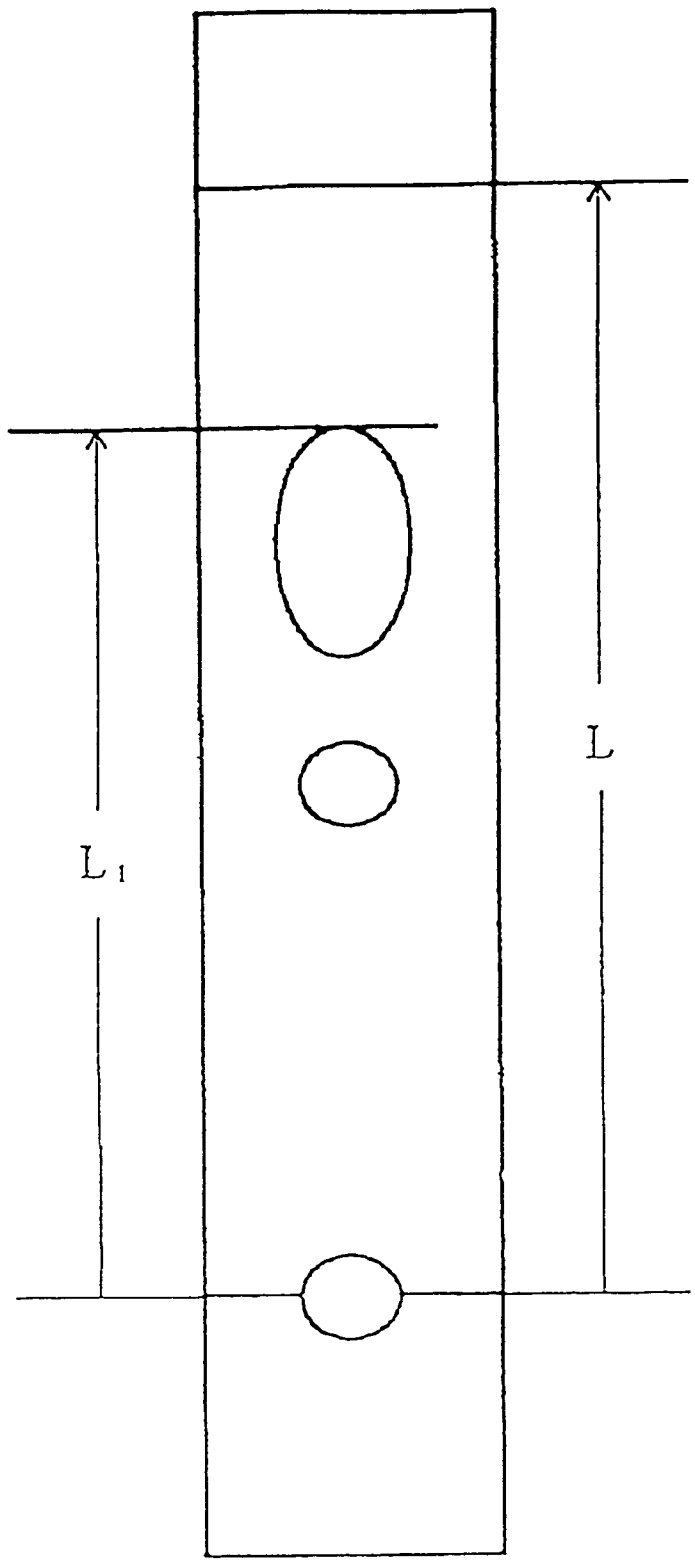
FIG. 2 is a model chart illustrating chromatogram obtained by thin layer chromatography.

Referring to an example of analysis by thin layer chromatography, 50 mg of the sample is dissolved in 1 g of chloroform to prepare a sample solution. Subsequently, from 0.2 to 1 $\mu$l of the sample solution is spotted on the thin layer plate at the position of 2 cm above the bottom thereof (original point) using a graduated capillary. The thin layer plate thus spotted is then thoroughly dried with nitrogen gas. The developing solvent prepared as mentioned above is put in a thin layer chromatography developing container to a depth of from 0.5 to 1 cm. The thin layer plate thus spotted is then slowly put into the thin layer chromatography developing container in such a manner that the original point is not dipped in the developing solvent. The developing container is then covered by a lid. The thin layer plate is then allowed to stand until the forward end of the solvent rising along the thin layer plate reaches the line of 1 cm from the upper end of the thin layer plate. Subsequently, the thin layer plate is withdrawn from the developing container, thoroughly dried with nitrogen gas, and then put in a color development container filled with iodine where it is then allowed to stand for 10 minuets. The thin layer plate is withdrawn from the color development container, and then readily measured for data of various spots. FIG. 2 is a model chart illustrating chromatogram obtained by thin layer chromatography. Rf value of thin layer chromatogram is obtained by dividing the distance $L_1$ between the original point and the main spot having the maximum (area×density) value by the developing distance L of the solvent.

$$Rf\ \text{value}=L_1/L$$

The data read by the densitometer is then subjected to image analysis to determine (area×density) value for various spots from which the purity of the main component is then calculated. As the densitometer there may be used , e.g., TLC scanner 3 produced by CAMAG Inc. As the analysis soft there may be used (CATS) software or the like.

In the oxirane derivative of the present invention, the number of moles of oxirane added PtopEOmol determined by the following equation:

$$P\text{top}EO\text{mol}=(P\text{top}Mw-ROHMw)/44$$

supposing that the molecular weight corresponding to the top of the peak on chromatogram is PtopMw and the molecular weight of the compound ROH is ROHMW, satisfies the following relationship with the ratio PMmw/mn of weight-average molecular weight to number-average molecular weight of the region represented by PareaM determined by gel permeation chromatography:

$$PM\text{mw}/\text{mn}-[1+P\text{top}EO\text{mol}/(1+P\text{top}EO\text{mol})^2]\leq 0.02,$$

preferably $$PM\text{mw}/\text{mn}-[1+P\text{top}EO\text{mol}/(1+P\text{top}EO\text{mol})^2]\leq 0.015.$$

When the value of PMmw/mn−[1+PtopEOmol/(1+PtopEOmol)$^2$] is small, it means that the resulting oxirane derivative has a polydispersion degree showing good approximation to Poisson distribution equation and hence little deviation from Poisson distribution of molecular weight of oxirane derivative. If this value exceeds 0.02, the resulting oxirane derivative can exhibit an insufficient homogeneity as starting material for medical purposes.

The oxirane derivative of the present invention is obtained by reacting the compound ROH with oxirane with the water content in the reaction system being not more than 5 ppm. If the compound ROH is an aliphatic alcohol, the reaction system is washed with a solvent showing azeotropy with water such as ethanol, dehydrated and dried at a temperature of from 80° C. to 150° C. under a pressure of 50 mmHg for 2 hours, and then subjected to distillation with a dehydrating agent such as metallic sodium so that it is dehydrated. The distilled alcohol is then used as a starting material. The starting material can then be continuously reacted with oxirane at a temperature of from 50° C. to 130° C., preferably from 80° C. to 120° C., in dried nitrogen gas in the presence of an alkaline catalyst with which the water content in the reaction system is reduced to not more than 5 ppm. Examples of the alkaline catalyst employable herein include metallic sodium, metallic potassium, alkoxide of compound ROH, and solution of compound ROH. For the preparation of oxirane derivative, Lewis acid catalysts such as boron trifluoride and tin tetrachloride are normally used besides the foregoing alkaline catalysts. However, if such an acid catalyst is used to obtain a high molecular compound of the present invention, a cyclic monomer such as 1,4-dioxane or cyclic polyether can be produced, making it difficult to obtain the desired compound at a desired purity to disadvantage. Further, if it is expected that the desired oxirane derivative has so high a molecular weight that the reaction system exhibits a raised viscosity at the latter stage of reaction, making it difficult to stir the reaction system, the reduction of the water content in the reaction system to not more than 5 ppm can be followed by the addition of an organic solvent having a boiling point of not lower than 50° C. free of functional group reactive with oxirane which has been distilled with a dehydrating agent such as metallic sodium and capable of dissolving the desired oxirane derivative therein, such as benzene, toluene and xylene in an amount of from 10 to 1,000%, preferably from 50 to 200% of that of the desired oxirane derivative, that causes addition reaction of oxirane.

If the compound ROH is an aromatic alcohol, the following preparation process can be used besides the foregoing process. In some detail, the reaction system is washed with a solvent azeotropic with water such as ethanol, and then dehydrated and dried at a temperature of from 80° C. to 150° C. under a pressure of not higher than 50 mmHg for 1 hour or longer. The compound ROH and a metallic alkoxide catalyst such as sodium methoxide, potassium methoxide and potassium t-butoxide which is optionally diluted with a low boiling solvent having a boiling point of not higher than 90° C. such as methanol, ethanol and t-butanol are then put in the reaction system. The reaction system is then treated at a temperature of not higher than 80° C. under a pressure of not higher than 50 mmHg in an atmosphere of dried nitrogen gas so that the diluting gas is removed while a slight amount of water content which has possibly entered into the system is being azeotropically removed to reduce the water content in the reaction system to not more than 5 ppm. Under these conditions, the compound ROH can then be continuously reacted with oxirane at a temperature of from 50° C. to 130° C., preferably from 80° C. to 120° C. in the presence of dried nitrogen gas.

Moreover, if the desired oxirane derivative has so high a molecular weight that the viscosity of the reaction system is raised at the latter stage of reaction, making it difficult to stir the reaction system, the reduction of the water content can be followed by the addition of an organic solvent having a boiling point of not lower than 50° C. free of functional group reactive with oxirane which has been distilled with a dehydrating agent such as metallic sodium and capable of dissolving the desired oxirane derivative therein, such as benzene, toluene and xylene in an amount of from 10 to 1,000%, preferably from 50 to 200% of that of the desired oxirane derivative, that causes addition reaction of oxirane.

Another embodiment of the oxirane derivative of the present invention has a structure represented by the following general formula [2]:

$$RO(C_2H_4O)n\text{-}Xp\text{-}Y \qquad [2]$$

wherein R represents a $C_{1-7}$ hydrocarbon group; n represents an integer of from 20 to 900; X represents a $C_{1-3}$ hydrocarbon group or —$CO(CH_2)q$— (in which q is an integer of from 2 to 4); Y represents an amino group or carboxyl group; and p represents an integer or 0 or 1. An example of the $C_{1-3}$ hydrocarbon group is a $C_{1-3}$ alkylene group. X is preferably a $C_{2-3}$ alkylene group. q is preferably 2 or 3.

The oxirane derivative of the present invention represented by the general formula [2] can be prepared from an oxirane derivative represented by the general formula [1]: $RO(C_2H_4O)nH$ which exhibits PareaM/Parea of not less than 0.85 in gel permeation chromatogram and shows main spots having a purity of not less than 98% in thin layer chromatogram. The compound represented by the general formula [1] to be used as a starting material preferably exhibits PareaH/Parea of not more than 0.05 and PMmw/mn-[1+PtopEomol/(1+PtopEOmol)$^2$] of not more than 0.02.

In the present invention, the process for the preparation of the oxirane derivative represented by the general formula [2] is not specifically limited. The oxirane derivative represented by the general formula [2] can be prepared by any known synthesis process. For example, the oxirane derivative represented by the general formula [2] wherein X is —$COCH_2CH_2$— and Y is a carboxylic acid can be prepared by reacting the oxirane derivative represented by the general formula [1] with succinic anhydride. The reaction of the oxirane derivative represented by the general formula [1] with succinic anhydride can be effected in the absence of catalyst or in the presence of organic amine, alkaline metal, alcoholate or alkaline metal or hydroxide of alkaline metal as a catalyst. For this reaction, a reaction solvent such as chloroform, benzene and toluene may be used. The reaction is effected at a temperature of preferably from 80° C. to 150° C. if effected in the absence of catalyst or from 40° C. to 130° C. if effected in the presence of catalyst.

The oxirane derivative represented by the general formula [2] wherein X is a methylene group and Y is a carboxyl group can be prepared by reacting an oxirane derivative represented by the general formula [1] with a halogenated acetic acid or derivative thereof such as monochloroacetic acid, monobromoacetic acid, sodium or potassium salt thereof, and methyl ester and ethyl ester thereof. The reaction is preferably effected at a temperature of from 80° C. to 150° C. in the presence of an alkaline metal, alcoholate of alkaline metal or hydroxide of alkaline metal as a catalyst. For this reaction, a reaction solvent such as toluene may be used. If an ester is used as a derivative of halogenated acetic acid, the reaction product of an oxirane derivative represented by the general formula [1] and the halogenated acetic acid ester can be saponified with an alkaline aqueous solution to obtain an oxirane derivative represented by the general formula [2] wherein Y is a carboxyl group. After the end of reaction, the reaction system can be adjusted for pH with a mineral acid such as hydrochloric acid and sulfuric acid, and then dehydrated under reduced pressure so that excessive alkaline catalyst is precipitated in the form of neutralized salt which can then be removed by filtration. Further, if a high purity compound is needed, the oxirane derivative thus obtained can be allowed to pass through a column filled with an ion-exchange resin so that the oxirane derivative represented by the general formula [2] is adsorbed by the ion-exchange resin while unreacted oxirane derivative represented by the general formula [1] is discharged out of the column. Thereafter, the oxirane derivative represented by the general formula [2] can be desorbed from the ion-exchange resin under weakly acidic conditions, and then dehydrated to obtain an oxirane derivative represented by the general formula at a high purity.

The oxirane derivative represented by the general formula [2] wherein X is an ethylene group and Y is a carboxyl group can be obtained by a process which comprises reacting an oxirane derivative represented by the general formula with acrylonitrile so that it is cyanoethylated, converting the cyano group in the cyanoethylated oxirane derivative to amide group under acidic conditions with hydrochloric acid, and then treating the material with an alkali such as sodium hydroxide to produce an alkaline salt of carboxylic acid. Further, if a high purity compound is needed, the oxirane derivative thus obtained can be allowed to pass through a column filled with an ion-exchange resin so that the oxirane derivative represented by the general formula [2] is adsorbed by the ion-exchange resin while unreacted oxirane derivative represented by the general formula [1] is discharged out of the column. Thereafter, the oxirane derivative represented by the general formula [2] can be desorbed from the ion-exchange resin under weakly acidic conditions, and then dehydrated to obtain an oxirane derivative represented by the general formula at a high purity.

The oxirane derivative represented by the general formula [2] wherein X is a trimethylene group and Y is an amino group can be prepared by a process which comprises reacting an oxirane derivative represented by the general formula [1] with acrylonitrile so that it is cyanoethylated, and then hydrogenating the cyano group in the cyanoethylated oxirane derivative. The hydrogenated is preferably effected at a temperature of from 80° C. to 200° C. under a pressure of from 5 to 50 $kg/cm^2$ in the presence of a hydrogenating catalyst such as Raney nickel in ammonia gas. After the end of reaction, the catalyst is preferably removed by filtration. Further, if a high purity compound is needed, as shown in JP-A-8-165343, a high purity oxirane derivative represented by the general formula [2] can be obtained by a process which comprises cyanoethylating an oxirane derivative represented by the general formula [1] in such a manner that the substitution percentage of hydroxyl group is controlled low to prevent the production of polyacrylonitrile, hydrogenating the cyanoethylated oxirane derivative, removing the catalyst from the reaction system, allowing the oxirane derivative thus obtained to pass through a column filled with an ion-exchange resin so that the oxirane derivative represented by the general formula [2] is adsorbed by the ion-exchange resin while unreacted oxirane derivative represented by the general formula [1] is discharged out of the column, desorbing the oxirane derivative represented by the general formula [2] under weakly alkaline conditions, and then dehydrating the oxirane derivative thus desorbed.

The oxirane derivative represented by the general formula [2] is useful particularly as a chemical modifier for physiologically active substances. The oxirane derivative represented by the general formula [2] wherein Y is a carboxyl group can react with the amino group in the chemical structure of physologically active substances. The carboxyl group in the oxirane derivative represented by the general formula [2] and the amino group in physiologically active substances can undergo direct reaction with each other in the presence of a dehydrating agent. However, if the physiologically active substance to be reacted is a substance which can be readily modified such as enzyme and thus cannot be subjected to hard condition, an oxirane derivative obtained by reacting an oxirane derivative represented by the general formula [2] with an activator having carboxyl group such as hydroxy succinimide in the presence of a dehydrating agent such as dicyclohexylcarbodimide can be used as well. In this case, the physiologically active substance and the derivative thus obtained can be mixed in a buffer solution to undergo reaction.

Further, the oxirane derivative represented by the general formula [2] wherein Y is an amino group can react with the carboxyl group in the chemical structure of physiologically active substance. The amino group in the oxirane derivative represented by the general formula [2] and the carboxyl group in physiologically active substances can undergo direct reaction with each other in the presence of a dehydrating agent. However, if the physiologically active substance to be reacted is a substance which can be readily modified such as enzyme and thus cannot be subjected to hard condition, the oxirane derivative represented by the general formula [2] is preferably reacted with other compounds to undergo further derivation before reaction with such a physiologically active substance.

Further, the oxirane derivative represented by the general formula [2] can be used to modify the surface of carrier for drug delivery having a physiologically active substance such as liposome encapsulated therein. In this case, phosphatidylethanolamine as a kind of phospholipid constituting liposome may be reacted with an oxirane derivative represented by the general formula [2] wherein Y is an amino group with a spacer such as succinic acid interposed therebetween.

In these uses, it is sometimes necessary that the functional group represented by X or Y in the oxirane derivative represented by the general formula [2] be changed depending on the functional group in the material to be modified and physical properties, stability and purposes of the material to be modified. In this case, oxirane derivatives having structures other than represented by the general formula [2] may be properly selected depending on the purpose.

These oxirane derivatives can be prepared in accordance with the foregoing preparation process or other known preparation processes.

EXAMPLE

The present invention will be further described in the following examples.

Example 1

3 l of dehydrated toluene (reagent: water content of 2.8 ppm) was measured out in a 5 l autoclave equipped with a nitrogen gas blowing tube having a calcium chloride dehydration tube, an injection tube, an agitator and a thermometer. The dehydrated toluene was heated to 90° C. where it was then stirred for 30 minutes. The blow line and the charging line attached to the autoclave were then thoroughly washed. The total amount of toluene was then discharged out of the autoclave under nitrogen gas pressure. The atmosphere in these lines was then thoroughly purged and replaced by nitrogen gas until no toluene mist was observed. The reaction system was then dried at a temperature of 120° C.±10° C. under a pressure of not higher than 5 mmHg for 5 hours.

(Proof that the Water Content in the Reaction System is Not More than 5 ppm)

4 l of dehydrated toluene (water content: 2.8 ppm) was pressed into a 5 l autoclave under nitrogen gas pressure. The dehydrated toluene was then stirred for 30 minutes. The total amount of the dehydrated toluene was taken out by a pressure vessel which had been heated in a 150° C. constant temperature oven for 3 hours. Toluene thus withdrawn had a water content of 2.9 ppm. It was thus confirmed that the calculated water content of the reaction system was 0.1 ppm.

The atmosphere in the various lines was then thoroughly purged and replaced by nitrogen gas until no toluene mist was observed. The reaction system was then dried at a temperature of 120° C.±10° C. under a pressure of not higher than 5 mmHg for 5 hours.

(Preparation of Starting Material)

An agitator, a rectifying column, a thermometer, a condenser, a nitrogen gas blowing tube equipped with a calcium chloride drying tube, a thermometer for distillation, a 2 l four-neck flask, a forked pipe, and two 1 l eggplant type flasks were previously dried in a 130° C. constant temperature oven for 3 hours. They were then assembled into a distillation apparatus. 1 kg of dehydrated methanol [reagent produced by Kanto Chemical Co., Ltd.; water content: 98 ppm] was then measured out in the four-neck flask in the distillation apparatus thus assembled. Subsequently, 10 g of metallic sodium was put into the four-neck flask. The mixture was then stirred in an atmosphere of nitrogen gas until metallic sodium was completely dissolved in methanol. The mixture was then gradually heated in a mild stream of nitrogen gas to undergo simple distillation at ordinary pressure. 200 g of the initial distillate was taken out. 500 g of the main distillate was then collected. The dehydrated and distilled methanol thus obtained as main distillate had a water content of 0.5 ppm.

To 480 g (15 mol) of the dehydrated and distilled methanol thus obtained were then added 46 g (2 mol) of metallic sodium in an atmosphere of nitrogen gas. The mixture was then stirred until it completely dissolved. A small amount of clouding precipitate was pressure-filtered under nitrogen gas. As a result, a methanol solution of high purity sodium methoxide made of a mixture of 2 mol of sodium methoxide and 13 mol of methanol was prepared.

Dried nitrogen gas was blown into a 5 l autoclave so that the autoclave was cooled to not higher than 30° C. The reaction system pressure was then adjusted to 1.0 kg/cm$^2$ with nitrogen gas. Subsequently, 52.4 g of the methanol solution of high purity sodium methoxide was measured out in a syringe, and then pressed into the autoclave through the injection pipe.

The reaction system was then heated to 90° C. 1,980 g of oxirane was then continuously pressed into the autoclave through the injection pipe at a temperature of 100° C.±2° C. under a pressure of 3 kg/cm$^2$ with vigorous stirring. After the end of addition of oxirane, stirring was continued at 100° C.±2° C. for 5 hours. Subsequently, the reaction system was allowed to cool to 80° C. where it was then processed at a temperature of from 75° C. to 85° C. under a pressure of from 50 to 100 mmHg with nitrogen gas being blown thereinto for 1 hour. The total amount of the reaction mixture was withdrawn, adjusted to pH 7.0 with a 1 N hydrochloric acid, and then dehydrated at a temperature of from 75° C. to 85° C. under a pressure of from 50 to 100 mmHg in an atmosphere of nitrogen gas. The resulting neutral salt wast hen removed by filtration to obtain 1,950 g of methoxy polyoxirane.

Figure 3:
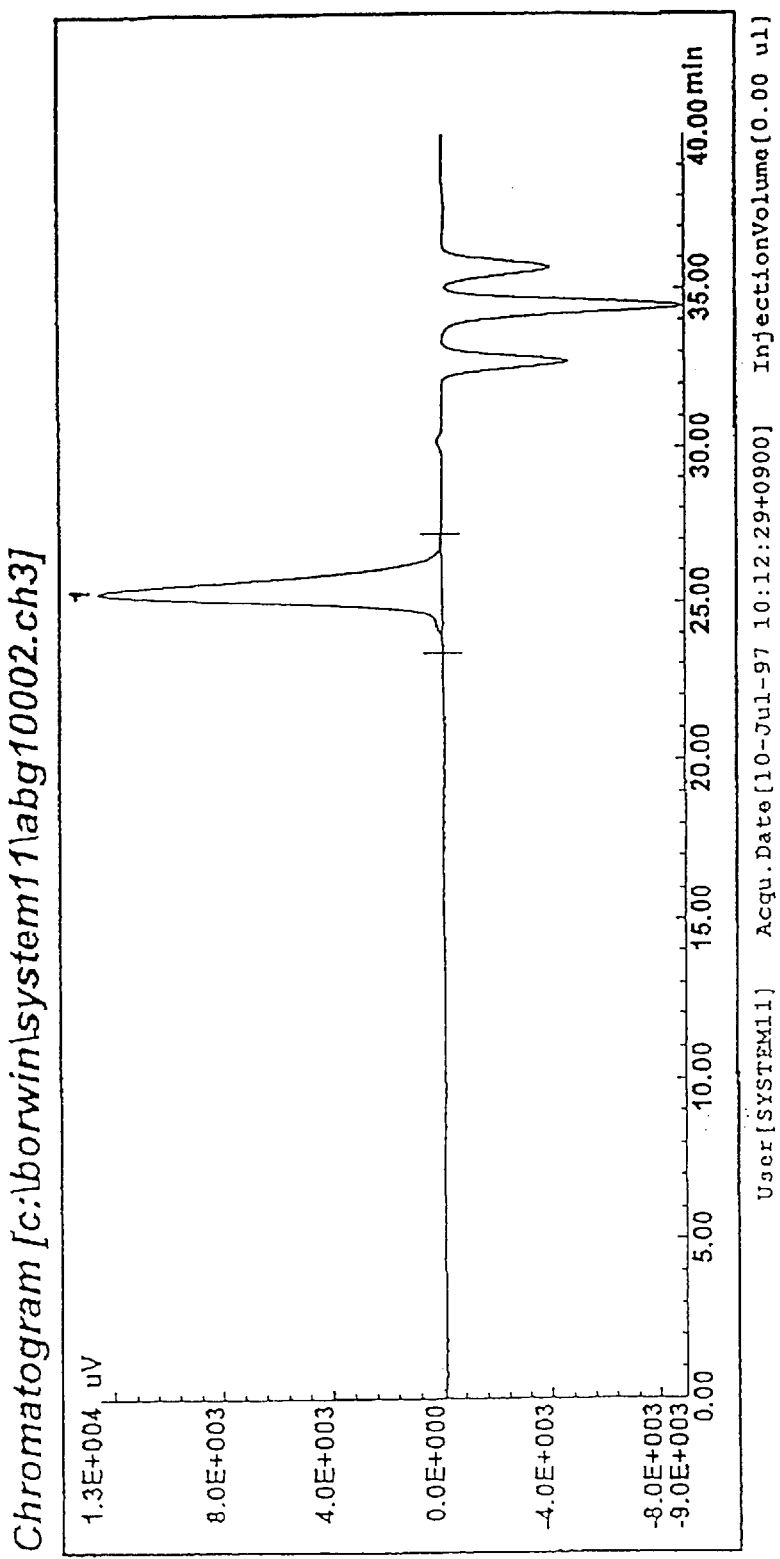
FIG. 3 illustrates the gel permeation chromatogram of a methoxy polyoxirane of Example 1.

The reaction product thus obtained was then measured by gel permeation chromatography (GPC). For gel permeation chromatography herein, SHODEX GPC SYSTEM-11 was used as GPC system, SHODEX RI-71 was used as a differential refractometer and three columns of SHODEX KF804L (φ8 mm×300 mm) connected in series were used as a GPC column. Tetrahydrofuran was allowed to flow at a rate of 1 ml/min as a developing solvent at a column temperature of 40° C. Under these conditions, 0.1 ml of a 0.1 wt-% specimen solution was then injected into the column. The resulting elution curve was then subjected to analysis by BORWIN GPC calculation program. The gel permeation chromatogram thus obtained is shown in FIG. 3. The data table showed that the retention time of the elution starting point is 23.375 minutes, the retention time of Ptop is 25.367 minutes, the retention time of two points at which the height of the elution curve from PbaseL is ⅕ of the height of PtopH are 24.829 minutes and 26.025 minutes, respectively, the retention time of the elution end point is 27.200 minutes, Parea is 643,168, PareaM is 585,895, and PareaH is 26,477. From these results, the following calculations were made:

$Parea M/Parea=0.911$ $Parea H/Parea=0.041$

Further, since PtopMw is 2,060, PMmw/mn is 1.0238 and PtopEOmol is 46.09, the following calculation can be made:

$PMmw/mn-[1+PtopEOmol/(1+PtopEOmol)^2]=0.003$

Figure 4:
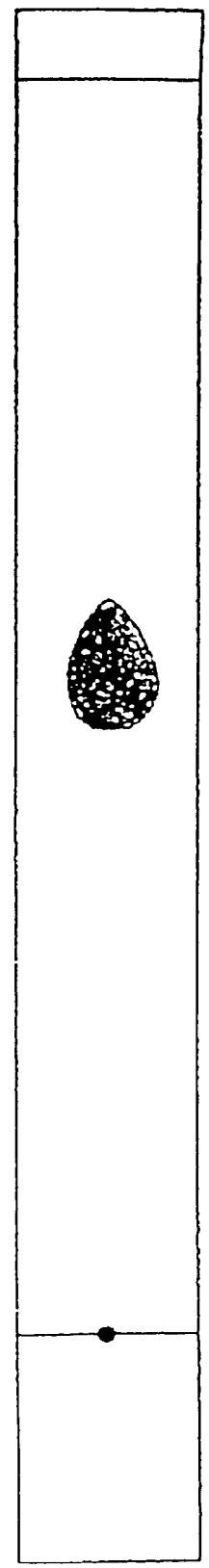
FIG. 4 illustrates the thin layer chromatogram of the methoxy polyoxirane of Example 1.

The reaction product thus obtained was also subjected to analysis by thin layer chromatography. As the glass thin layer plate there was used silica gel 60 laminate (Merck Japan Ltd.). As the developing solvent there was used a 85:15 mixture (by volume) of chloroform and methanol. The thin layer chromatogram thus obtained is shown in FIG. 4. The main component on the thin layer chromatogram thus obtained showed Rf value of 0.588. As a result of analysis by a densitometer, the main component showed a purity of 99.87% and hence an impurity content of 0.13%.

Example 2

An agitator, a rectifying column, a thermometer, a condenser, a nitrogen gas blowing tube equipped with a calcium chloride drying tube, a thermometer for distillation, a 2 l four-neck flask, a forked pipe, and two 1 l eggplant type flasks were previously dried in a 130° C. constant temperature oven for 3 hours. They were then assembled into a distillation apparatus. 4 kg of dehydrated toluene (reagent) was then measured out in the four-neck flask in the distillation apparatus thus assembled. Subsequently, 10 g of metallic sodium was put into the four-neck flask. The mixture was then stirred in an atmosphere of nitrogen gas for 3 hours. The mixture was then gradually heated in a mild stream of nitrogen gas to undergo simple distillation at ordinary pressure. 480 g of the initial distillate was taken out. 2,120 g of the main distillate was then collected. The dehydrated and purified toluene thus obtained as main distillate had a water content of 0.1 ppm.

Dried nitrogen gas was blown into a 5 l autoclave which had been cleaned and dried in the same manner as in Example 1 so that the autoclave was cooled to not higher than 30° C. The system pressure was then adjusted to 1.0 kg/cm² with nitrogen gas. Subsequently, 21.0 g of the methanol solution of high purity sodium methoxide prepared in Example 1 was measured out in a syringe, and then pressed into the autoclave through the injection pipe. 750 g of dehydrated and purified toluene prepared above was measured out in a syringe in such a manner that it didn't come in contact with air, and then pressed into the autoclave through the injection pipe.

The reaction system was then heated to 90° C. 2,238 g of oxirane was then continuously pressed into the autoclave through the injection pipe at a temperature of 110° C.±2° C. under a pressure of 3 kg/cm² with vigorous stirring. After the end of addition of oxirane, stirring was continued at 100° C.±2° C. for 5 hours. Subsequently, the reaction system was allowed to cool to 80° C. where it was then processed at a temperature of from 75° C. to 85° C. under a pressure of from 50 to 100 mmHg with nitrogen gas being blown thereinto for 1 hour. The total amount of the reaction mixture was withdrawn, adjusted to pH 7.0 with a 1 N hydrochloric acid, and then dehydrated and desolvated at a temperature of from 75° C. to 85° C. under a pressure of from 50 to 100 mmHg in an atmosphere of nitrogen gas. The resulting neutral salt was then removed by filtration to obtain 2,140 g of methoxy polyoxirane.

Figure 5:
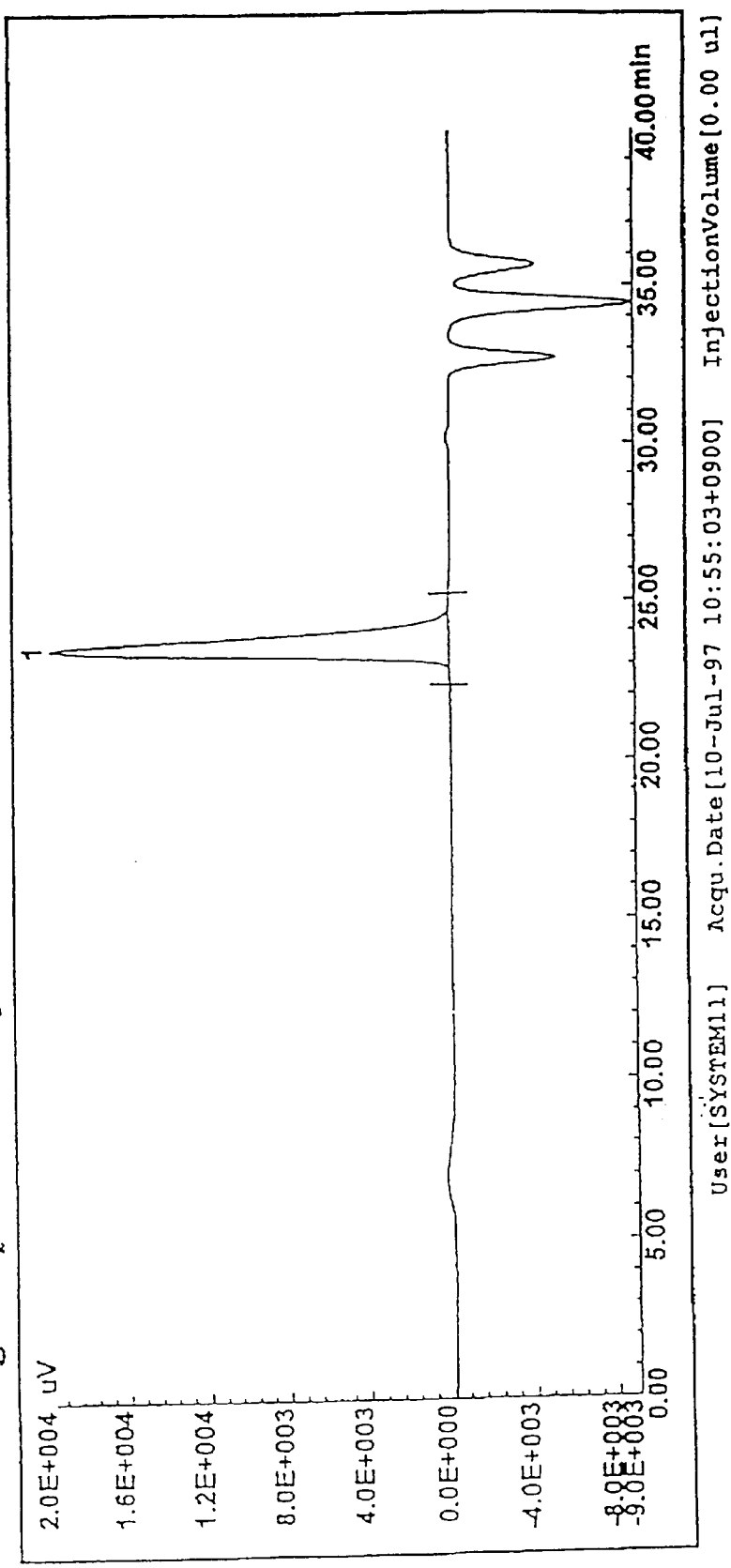
FIG. 5 illustrates the gel permeation chromatogram of a methoxy polyoxirane of Example 2.

The reaction product thus obtained was then measured by GPC in the same manner as in Example 1. The gel permeation chromatogram thus obtained is shown in FIG. 5. The data table showed that the retention time of the elution starting point is 22.500minutes, the retention time of Ptop is 23.542 minutes, the retention time of two points at which the height of the elution curve from PbaseL is ⅕ of the height of PtopH are 23.163 minutes and 24.088 minutes, respectively, the retention time of the elution end point is 25.217 minutes, Parea is 769,726, PareaM is 706,513, and PareaH is 16,731. From these results, the following calculations can be made:

$$PareaM/Parea=0.918$$

$$PareaH/Parea=0.022$$

Further, since PtopMw is 5,800, PMmw/mn is 1.0151 and PtopEOmol is 131.09, the following calculation can be made:

$$PMmw/mn-[1+PtopEOmol/(1+PtopEOmol)^2]=0.008$$

The reaction product thus obtained was also subjected to analysis by thin layer chromatography in the same manner as in Example 1. The main component on the thin layer chromatogram thus obtained showed Rf value of 0.532. As a result of analysis by a densitometer, the main component showed a purity of 99.6% and hence an impurity content of 0.4%.

Example 3

Dried nitrogen gas was blown into a 5 l autoclave which had been cleaned and dried in the same manner as in Example 1 so that the autoclave was cooled to not higher than 30° C. The system pressure was then adjusted to 1.0 kg/cm² with nitrogen gas. Subsequently, 10.48 g of the methanol solution of high purity sodium methoxide prepared in Example 1 was measured out in a syringe, and then pressed into the autoclave through the injection pipe. 1,200 g of dehydrated and purified toluene prepared in Example 2 was measured out in a syringe in such a manner that it didn't come in contact with air, and then pressed into the autoclave through the injection pipe.

The reaction system was then heated to 90° C. 2,400 g of oxirane was then continuously pressed into the autoclave through the injection pipe at a temperature of 110° C.±2° C. under a pressure of 3 kg/cm² with vigorous stirring. After the end of addition of oxirane, stirring was continued at 110° C.±2° C. for 5 hours. Subsequently, the reaction system was allowed to cool to 80° C. where it was then processed at a temperature of from 75° C. to 85° C. under a pressure of from 50 to 100 mmHg with nitrogen gas being blown thereinto for 1 hour. The total amount of the reaction mixture was withdrawn, adjusted to pH 7.0 with a 1 N hydrochloric acid, and then dehydrated and desolvated at a temperature of from 75° C. to 85° C. under a pressure of from 50 to 100 mmHg in an atmosphere of nitrogen gas. The resulting neutral salt was then removed by filtration to obtain 2,256 g of methoxy polyoxirane.

Figure 6:
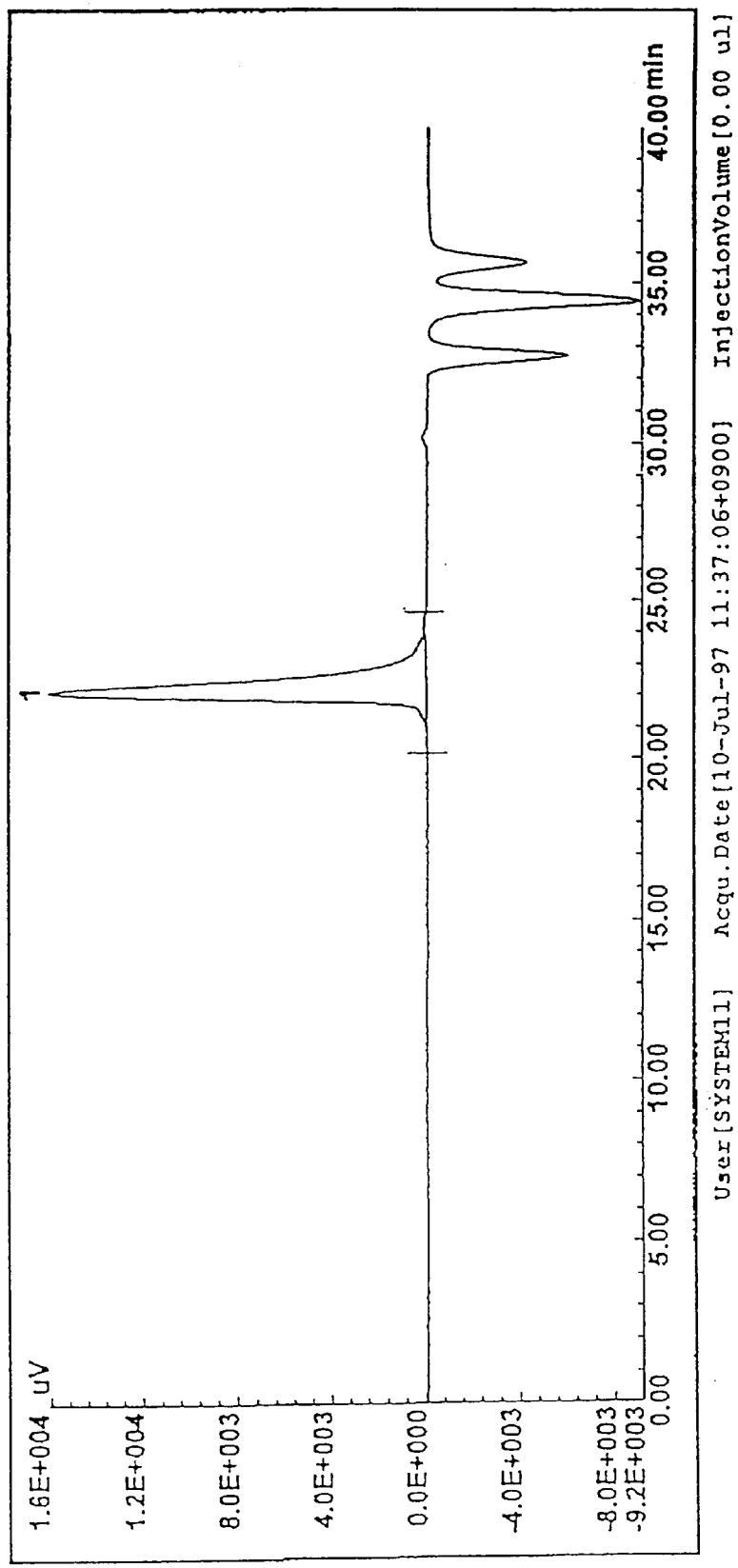
FIG. 6 illustrates the gel permeation chromatogram of a methoxy polyoxirane of Example 3.

The reaction product thus obtained was then measured by GPC in the same manner as in Example 1. The gel permeation chromatogram thus obtained is shown in FIG. 6. The data table showed that the retention time of the elution starting point is 20.200 minutes, the retention time of Ptop is 22.117 minutes, the retention time of two points at which the height of the elution curve from PbaseL is ⅕ of the height of PtopH are 21.775 minutes and 22.767 minutes, respectively, the retention time of the elution end point is 24.617 minutes, Parea is 638,118, PareaM is 605,970, and PareaH is 17,853. From these results, the following calculations can be made:

$$PareaM/Parea=0.887$$

$$PareaH/Parea=0.026.$$

Further, since PtopMw is 12,730, PMmw/mn is 1.0164 and PtopEOmol is 288.59, the following calculation can be made:

$$PMmw/mn-[1+PtopEOmol/(1+PtopEOmol)^2]=0.013$$

The reaction product thus obtained was also subjected to analysis by thin layer chromatography in the same manner as in Example 1. The main component on the thin layer chromatogram thus obtained showed Rf value of 0.442. As a result of analysis by a densitometer, the main component showed a purity of 99.2% and hence an impurity content of 0.8%.

Example 4

1,450 g of dehydrated and purified toluene (water content: 0.2 ppm) was prepared in the same manner as in Example 2. (Preparation of Starting Material)

An agitator, a rectifying column, a thermometer, a condenser, a nitrogen gas blowing tube equipped with a calcium chloride drying tube, a thermometer for distillation, a 2 l four-neck flask, a forked pipe, and two 1 l eggplant type flasks were previously dried in a 130° C. constant temperature oven for 3 hours. They were then assembled into a distillation apparatus. 3 kg of dehydrated ethanol (reagent) was then measured out in the four-neck flask in the distillation apparatus thus assembled. Subsequently, 10 g of metallic sodium was put into the four-neck flask. The mixture was then stirred in an atmosphere of nitrogen gas until metallic sodium was completely dissolved in ethanol. The mixture was then gradually heated in a mild stream of nitrogen gas to undergo simple distillation at ordinary pressure. 450 g of the initial distillate was taken out. 1,820 g of the main distillate was then collected. The dehydrated and distilled ethanol thus obtained as main distillate had a water content of 0.2 ppm.

To 690 g (15 mol) of the dehydrated and distilled ethanol thus obtained were then added 46 g (2 mol) of metallic sodium in an atmosphere of nitrogen gas. The mixture was then stirred until it completely dissolved. A small amount of clouding precipitate was pressure-filtered under nitrogen gas. As a result, an ethanol solution of high purity sodium ethoxide made of a mixture of 2 mol of sodium ethoxide and 13 mol of ethanol was prepared.

Dried nitrogen gas was blown into a 5 l autoclave which had been cleaned and dried in the same manner as in Example 1 so that the autoclave was cooled to not higher than 30° C. The system pressure was then adjusted to 1.0 kg/cm$^2$ with nitrogen gas. Subsequently, 7.34 g of the ethanol solution of high purity sodium ethoxide was measured out in a syringe, and then pressed into the autoclave through the injection pipe.

The reaction system was then heated to 90° C. 2,016 g of oxirane was then continuously pressed into the autoclave through the injection pipe at a temperature of 110° C.±2° C. under a pressure of 4 kg/cm2 with vigorous stirring. After the end of addition of oxirane, stirring was continued at 110° C.±0.2° C. for 5 hours. Subsequently, the reaction system was allowed to cool to 80° C. where it was then processed at a temperature of from 75° C. to 85° C. under a pressure of from 50 to 100 mmHg with nitrogen gas being blown thereinto for 1 hour. The total amount of the reaction mixture was withdrawn, adjusted to pH 7.0 with a 1 N hydrochloric acid, and then dehydrated at a temperature of from 75° C. to 85° C. under a pressure of from 50 to 100 mmHg in an atmosphere of nitrogen gas. The resulting neutral salt was then removed by filtration to obtain 1,905 g of methoxy polyoxirane.

Figure 7:
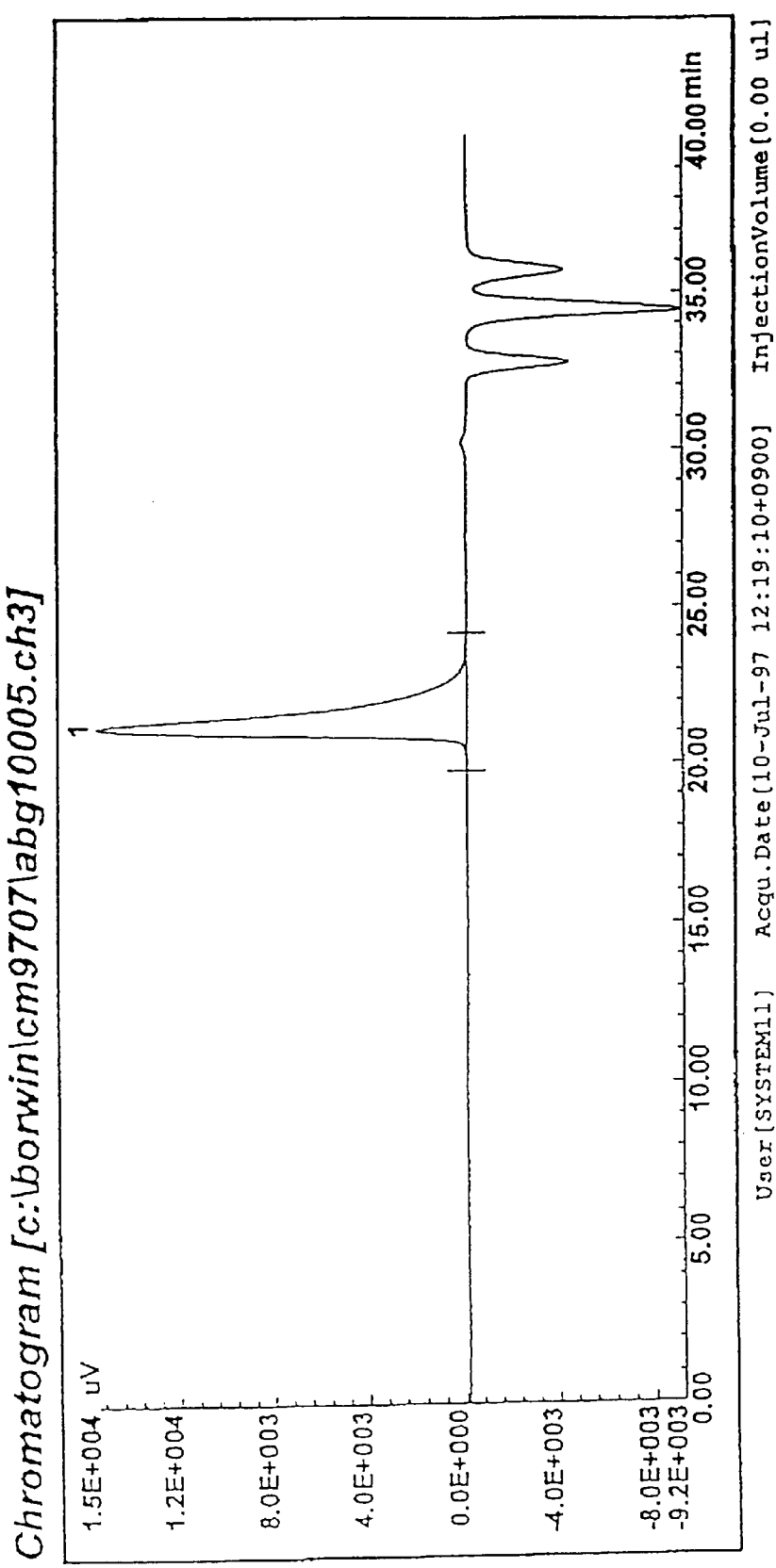
FIG. 7 illustrates the gel permeation chromatogram of an ethoxy polyoxirane of Example 4.

The reaction product thus obtained was then measured by GPC in the same manner as in Example 1. The gel permeation chromatogram thus obtained is shown in FIG. 7. The data table showed that the retention time of the elution starting point is 19.800 minutes, the retention time of Ptop is 21.158 minutes, the retention time of two points at which the height of the elution curve from PbaseL is 1/5 of the height of PtopH are 20.813 minutes and 22.017 minutes, respectively, the retention time of the elution end point is 24.133 minutes, Parea is 772,936, PareaM is 678,333, and PareaH is 17,510. From these results, the following calculations were made:

$PareaM/Parea=0.878$ $PareaH/Parea=0.023$

Further, since PtopMw is 20,861, PMmw/mn is 1.0223 and PtopEOmol is 473.07, the following calculation can be made:

$PMmw/mn-[1+PtopEOmol/(1+PtopEOmol)^2]=0.020$

The reaction product thus obtained was also subjected to analysis by thin layer chromatography in the same manner as in Example 1. The main component on the thin layer chromatogram thus obtained showed Rf value of 0.412. As a result of analysis by a densitometer, the main component showed a purity of 98.9% and hence an impurity content of 1.1%.

Example 5

Dried nitrogen gas was blown into a 5 l autoclave which had been cleaned and dried in the same manner as in Example 1 so that the autoclave was cooled to not higher than 30° C. The system pressure was then adjusted to 1.0 kg/cm$^2$ with nitrogen gas. Subsequently, 108.1 g of benzyl alcohol [purity: 99.9% by weight; water content: 1,350 ppm; reagent produced by Kanto Chemical Co., Ltd.] and 300 g of dehydrated and distilled methanol prepared in Example 1 were put into the autoclave. The mixture was then dehydrated and desolvated at a temperature of from 55° C. to 70° C. under a pressure of 10 to 50 mmHg in an atmosphere of nitrogen gas for 3 hours. Subsequently, the interior of the autoclave was compressed under a pressure of 0.5 kg/cm$^2$ with dried nitrogen gas. 43.2 g of a specimen to be measured for water content was withdrawn from the autoclave at the bottom valve, and then measured for water content. The results were 2.3 ppm.

Into the autoclave were then put 4.8 g of sodium methoxide [produced by TOSOH CORP.] and 200 g of dehydrated and distilled methanol prepared in Example 1. The mixture was then dehydrated and desolvated at a temperature of from 55° C. to 70° C. under a pressure of from 10 to 50 mmHg in an atmosphere of nitrogen gas for 5 hours. Subsequently, the interior of the autoclave was compressed at a 1.0 kg/cm$^2$ with dried nitrogen gas.

The reaction system was then heated to 90° C. 2,358 g of oxirane was then continuously pressed into the autoclave through the injection pipe at a temperature of 100° C.±2° C. under a pressure of 4 kg/cm$^2$ with vigorous stirring. After the end of addition of oxirane, stirring was continued at 100° C.±0.2° C. for 5 hours. Subsequently, the reaction system was allowed to cool to 80° C. where it was then processed at a temperature of from 75° C. to 85° C. under a pressure of from 50 to 100 mmHg with nitrogen gas being blown thereinto for 1 hour. The total amount of the reaction mixture was withdrawn, adjusted to pH 7.0 with a 1 N hydrochloric acid, and then dehydrated and desolvated at a temperature of from 75° C. to 85° C. under a pressure of from 50 to 100 mmHg in an atmosphere of nitrogen gas. The resulting neutral salt was then removed by filtration to obtain 2,293 g of benzyloxy polyoxirane.

Figure 8:
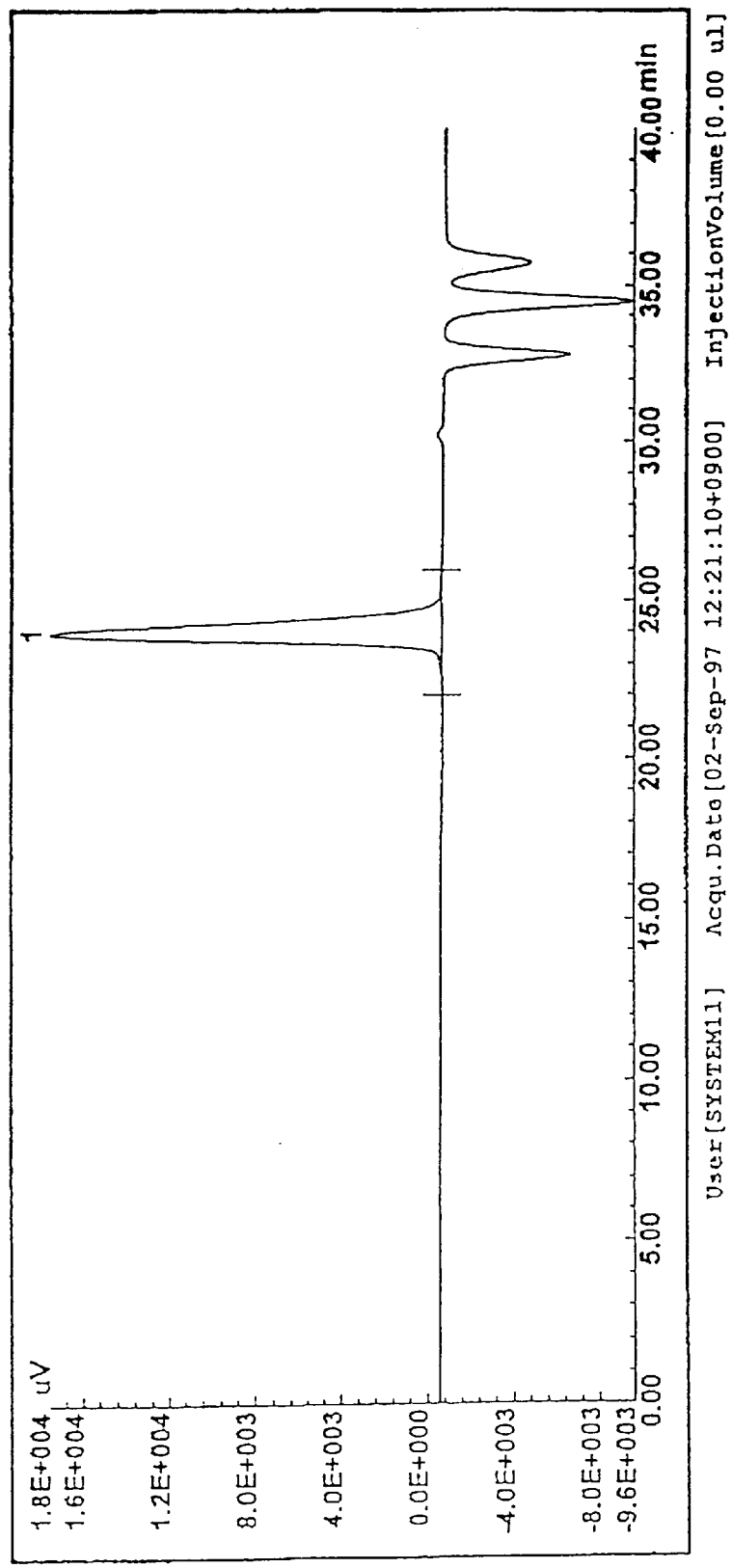
FIG. 8 illustrates the gel permeation chromatogram of a benzyloxy polyoxirane of Example 5.

The reaction product thus obtained was then measured by GPC in the same manner as in Example 1. The gel permeation chromatogram thus obtained is shown in FIG. 8. The data table showed that the retention time of the elution starting point is 22.050 minutes, the retention time of Ptop is 24.008 minutes, the retention time of two points at which the height of the elution curve from PbaseL is 1/5 of the height of PtopH are 23.608 minutes and 24.533 minutes, respectively, the retention time of the elution end point is 25.983 minutes, Parea is 717,393, PareaM is 656,946, and PareaH is 23,737. From these results, the following calculations can be made:

$PareaM/Parea=0.916$ $PareaH/Parea=0.033$

Further, since PtopMw is 4,442, PMmw/mn is 1.0155 and PtopEOmol is 98.49, the following calculation can be made:

$PMmw/mn-[1+PtopEOmol/(1+PtopEOmol)^2]=0.006$

The reaction product thus obtained was also subjected to analysis by thin layer chromatography in the same manner as in Example 1. The main component on the thin layer chromatogram thus obtained showed Rf value of 0.561. As a result of analysis by a densitometer, the main component showed a purity of 99.4% and hence an impurity content of 0.6%.

Comparative Example 1

Into a 5 l autoclave which had been cleaned and dried in the same manner as in Example 1 were put 28.8 g of (0.9 mol) of dehydrated methanol [reagent produced by Kanto Chemical Co., Ltd.; water content: 98 ppm] and 5.4 g (0.1 mol) of sodium methoxide (produced by TOSOH CORP.). The atmosphere in the autoclave was then rapidly replaced by nitrogen gas at a temperature of not higher than 30° C. 1,980 g of oxirane was then continuously pressed into the autoclave through the injection pipe at a temperature of 150° C.±10° C. under a pressure of 3 kg/cm² with vigorous stirring. After the end of addition of oxirane, stirring was continued at 150° C.±10° C. for 3 hours. Subsequently, the reaction system was allowed to cool to 80° C. where it was then processed at a temperature of from 75° C. to 85° C. under a pressure of from 50 to 100 mmHg with nitrogen gas being blown thereinto for 1 hour. The total amount of the reaction mixture was withdrawn, adjusted to pH 7.0 with a 1 N hydrochloric acid, and then dehydrated at a temperature of from 75° C. to 85° C. under a pressure of from 50 to 100 mmHg in an atmosphere of nitrogen gas. The resulting neutral salt was then removed by filtration to obtain 1,932 g of methoxy polyoxirane.

Figure 9:
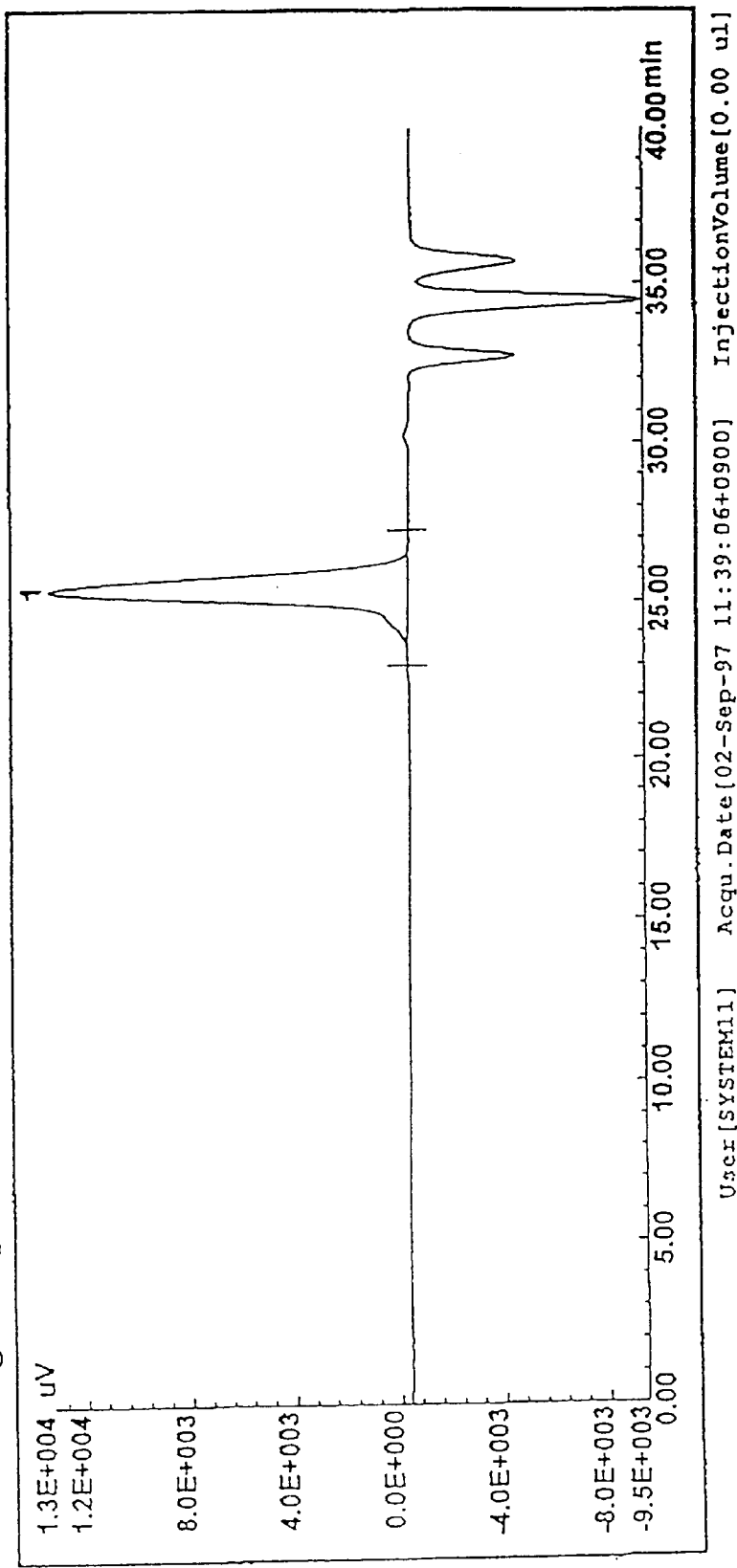
FIG. 9 illustrates the gel permeation chromatogram of a methoxy polyoxirane of Comparative Example 1.
Figure 10:
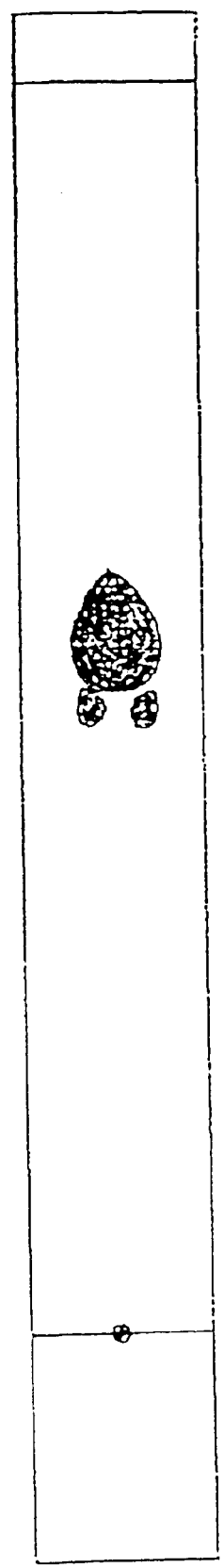
FIG. 10 illustrates the thin layer chromatogram of the methoxy polyoxirane of Comparative Example 1.

The reaction product thus obtained was then measured by GPC in the same manner as in Example 1. The gel permeation chromatogram thus obtained is shown in FIG. 9. The data table showed that the retention time of the elution starting point is 22.983 minutes, the retention time of Ptop is 25.417 minutes, the retention time of two points at which the height of the elution curve from PbaseL is ⅕ of the height of PtopH are 24.871 minutes and 26.021 minutes, respectively, the retention time of the elution end point is 27.233 minutes, Parea is 688,244, PareaM is 607,608, and PareaH is 55,817. From these results, the following calculations can be made:

$PareaM/Parea=0.883$ $PareaH/Parea=0.081$

Further, since PtopMw is 2,004, PMmw/mn is 1.0212 and PtopEOmol is 44.82, the following calculation can be made:

$PMmw/mn-[1+PtopEOmol/(1+PtopEOmol)^2]=0.0001$

The reaction product thus obtained was also subjected to analysis by thin layer chromatography in the same manner as in Example 1. The main component on the thin layer chromatogram thus obtained showed Rf value of 0. 608. As a result of analysis by a densitometer, the main component showed a purity of 96.23% and hence an impurity content of 3.77%.

Comparative Example 2

Benzyloxy polyoxirane was synthesized in accordance with a process for the synthesis of oxirane derivative which is generally practiced on an industrial basis. A 5 l autoclave was washed with soapy water, and then rinsed twice with 3 l of tap water. The autoclave was then thoroughly purged with nitrogen gas until no mist was observed.

Into the autoclave were then put 64.86 g of benzyl alcohol as used in Example 5 [produced by Kanto Chemical Co., Ltd.; purity: 99.9%; water content: 1,350 ppm] and 4.8 g of potassium hydroxide. The mixture was then dehydrated at a temperature of from 70° C. to 90° C. under a pressure of from 100 to 200 mmHg in an atmosphere of nitrogen gas for 0.5 hours. Subsequently, the interior of the autoclave was compressed at a pressure of 1.0 kg/cm² with nitrogen gas. The reaction system was then heated to 90° C. 2,568 g of oxirane was then continuously pressed into the autoclave through the injection pipe at a temperature of 150° C.±10° C. under a pressure of 4 kg/cm² with vigorous-stirring. After the end of addition of oxirane, stirring was continued at 150° C.±10° C. for 2 hours. Subsequently, the reaction system was allowed to cool to 80° C. where it was then processed at a temperature of from 75° C. to 85° C. under a pressure of from 50 to 100 mmHg with nitrogen gas being blown thereinto for 1 hour. The total amount of the reaction mixture was withdrawn, adjusted to pH 7.0 with a 1 N hydrochloric acid, and then dehydrated and desolvated at a temperature of from 75° C. to 85° C. under a pressure of from 50 to 100 mmHg in an atmosphere of nitrogen gas. The resulting neutral salt was then removed by filtration to obtain 2,475 g of benzyloxy polyoxirane.

Figure 11:
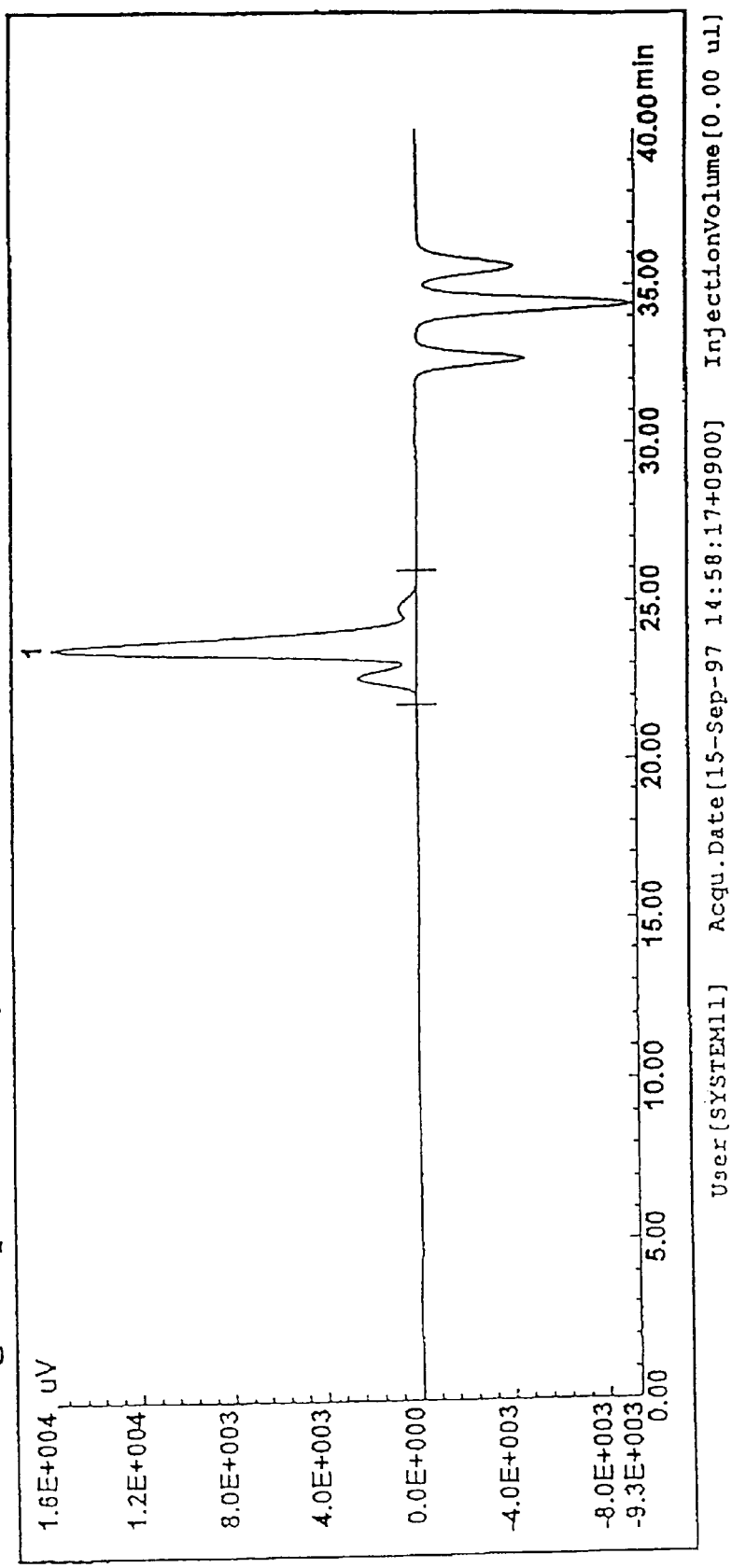
FIG. 11 illustrates the gel permeation chromatogram of a benzyloxy polyoxirane of Comparative Example 2.

The reaction product thus obtained was then measured by GPC in the same manner as in Example 1. The gel permeation chromatogram thus obtained is shown in FIG. 11. The data table showed that the retention time of the elution starting point is 21.758 minutes, the retention time of Ptop is 23.550 minutes, the retention time of two points at which the height of the elution curve from PbaseL is ⅕ of the height of PtopH are 23.183 minutes and 24.083 minutes, respectively, the retention time of the elution end point is 25.942 minutes, Parea is 690,474, PareaM is 536,228, and PareaH is 92,494. From these results, the following calculations can be made:

$PareaM/Parea=0.777$ $PareaH/Parea=0.134$

Further, since PtopMw is 5,859, PMmw/mn is 1.0137 and PtopEOmol is 130.70, the following calculation can be made:

$PMmw/mn-[1+PtopEOmol/(1+PtopEOmol)^2]=0.006$

The reaction product thus obtained was also subjected to analysis by thin layer chromatography in the same manner as in Example 1. The main component on the thin layer chromatogram thus obtained showed Rf value of 0.561. As a result of analysis by a densitometer, the main component showed a purity of 82.31% and hence an impurity content of 17.69%.

Comparative Example 3

Figure 12:
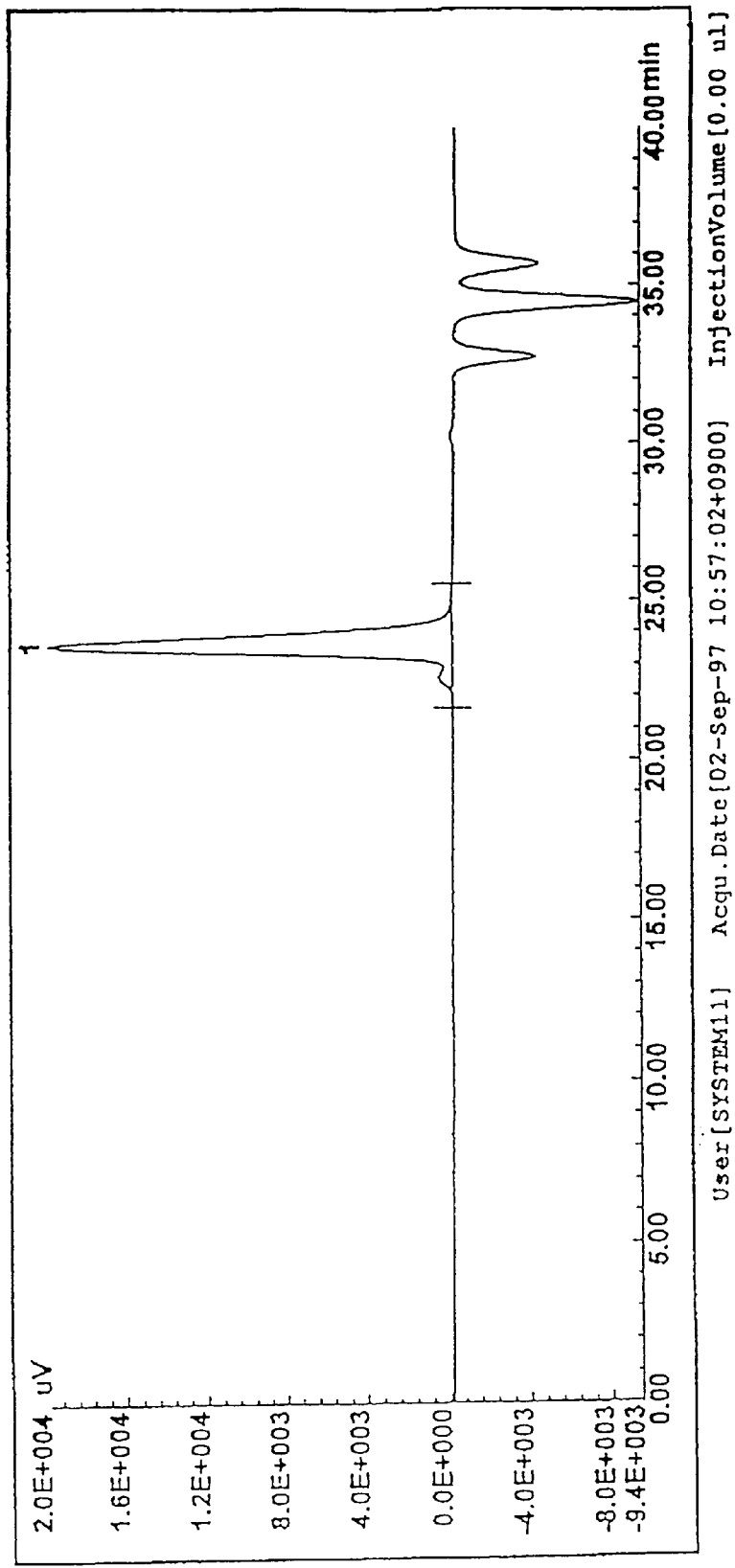
FIG. 12 illustrates the gel permeation chromatogram of the methoxy polyoxirane of Comparative Example 3.

A commercially available methoxy polyoxirane [reagent produced by Aldrich Corp.: poly(ethyleneglycol)methyl ether: Model No. 20, 251-7, Mw=5,000] was then measured by GPC in the same manner as in Example 1. The gel permeation chromatogram thus obtained is shown in FIG. 12. The data table showed that the retention time of the elution starting point is 21.650 minutes, the retention time of Ptop is 23.592 minutes, the retention time of two points at which the height of the elution curve from PbaseL is ⅕ of the height of PtopH are 23.204 minutes and 24.108 minutes, respectively, the retention time of the elution end point is 25.508 minutes, Parea is 790,168, PareaM is 707,655, and PareaH is 47,378. From these results, the following calculations can be made:

$PareaM/Parea=0.896$ $PareaH/Parea=0.060$

Further, since PtopMw is 5,638, PMmw/mn is 1.0150 and PtopEOmol is 127.4, the following calculation can be made:

$$PMmw/mn-[1+PtopEOmol/(1+PtopEOmol)^2]=0.007$$

The specimen was also subjected to analysis by thin layer chromatography in the same manner as in Example 1. The main component on the thin layer chromatogram thus obtained showed Rf value of 0.535. As a result of analysis by a densitometer, the main component showed a purity of 97.30% and hence an impurity content of 2.70%.

Comparative Example 4

Figure 13:
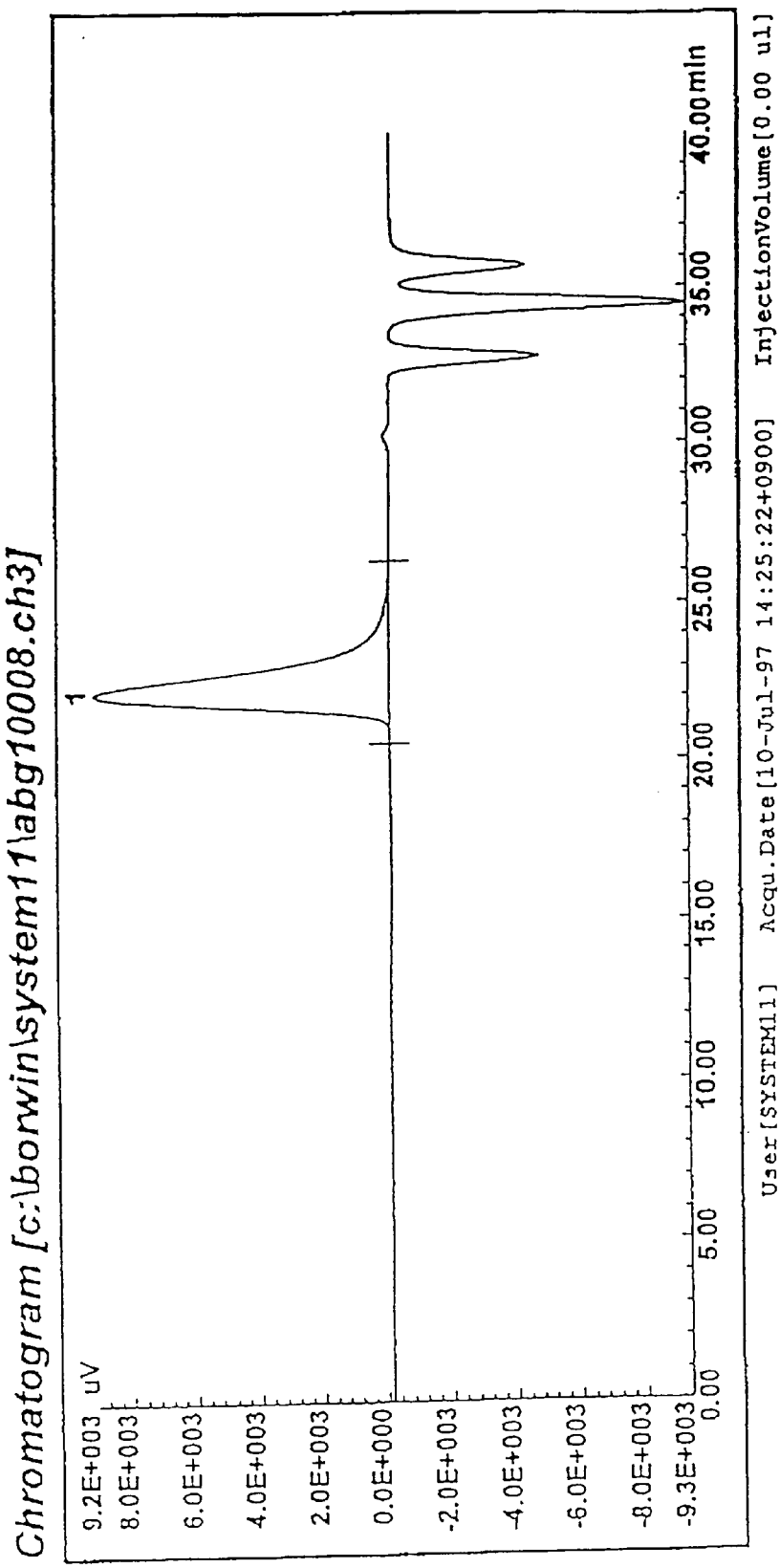
FIG. 13 illustrates the gel permeation chromatogram of a methoxy polyoxirane of Comparative Example 4.

A commercially available methoxy polyoxirane [Model No. Methoxy-PEGMP-12800; Mw: 12,800, produced by Polymer Laboratory Co., Ltd.] was then measured by GPC in the same manner as in Example 1. The gel permeation chromatogram thus obtained is shown in FIG. 13. The data table showed that the retention time of the elution starting point is 20.500 minutes, the retention time of Ptop is 22.150 minutes, the retention time of two points at which the height of the elution curve from PbaseL is ⅕ of the height of PtopH are 21.553 minutes and 25.558 minutes, respectively, the retention time of the elution termination point is 26.333 minutes, Parea is 694,471, PareaM is 617,697, and PareaH is 13,759. From these results, the following calculations can be made:

$$PareaM/Parea=0.889$$

$$PareaH/Parea=0.020$$

Further, since PtopMw is 12,507, PMmw/mn is 1.0527 and PtopEOmol is 283.52, the following calculation can be made:

$$PMmw/mn-[1+PtopEOmol/(1+PtopEOmol)^2]=0.049$$

The specimen was also subjected to analysis by thin layer chromatography in the same manner as in Example 1. The main component on the thin layer chromatogram thus obtained showed Rf value of 0.439. As a result of analysis by a densitometer, the main component showed a purity of 96.90% and hence an impurity content of 3.10%.

The results of Examples 1 to 5 and Comparative Examples 1 to 4 are altogether set forth in Table 1 below.

TABLE 1

| | Gel permeation chromatography | | | thin layer chromatography | |
| --- | --- | --- | --- | --- | --- |
| | PareaM/ Parea | PareaH/ Parea | A (*1) | Rf value | Purity of main spot (%) |
| Example 1 | 0.911 | 0.041 | 0.003 | 0.588 | 99.87 |
| Example 2 | 0.918 | 0.022 | 0.008 | 0.532 | 99.6 |
| Example 3 | 0.887 | 0.026 | 0.013 | 0.442 | 99.2 |
| Example 4 | 0.878 | 0.023 | 0.020 | 0.412 | 98.9 |
| Example 5 | 0.916 | 0.033 | 0.006 | 0.561 | 99.4 |
| Comparative Example 1 | 0.883 | 0.081 | 0.0001 | 0.608 | 96.23 |
| Comparative Example 2 | 0.777 | 0.134 | 0.006 | 0.561 | 82.31 |
| Comparative Example 3 | 0.896 | 0.060 | 0.007 | 0.535 | 97.30 |
| Comparative Example 4 | 0.889 | 0.020 | 0.049 | 0.439 | 96.90 |

[Note]
(*1) PMmw/mn − [1 + PtopEOmol/(1 + PtopEOmol)$^2$]

Example 6

An oxirane derivative for modifying chemical was synthesized from the methoxy polyoxirane (Mw=5,800) prepared in Example 2.

In some detail, 58.0 g (0.01 mol) of the methoxy polyoxirane (Mw=5,800), 300 ml of toluene and 1.3 g (0.013 mol) of succinic anhydride were put into a 1 l four-neck flask equipped with a nitrogen gas blowing tube, an agitator, a condenser and a thermometer. The reaction mixture was then heated to 80° C. with stirring in a stream of nitrogen gas. To the reaction mixture was then added 1.00 g (0.01 mol) of triethylamine. The reaction mixture was then gradually heated until it was refluxed. Refluxing was continued for 3 hours. Subsequently, the reaction solution was desolvated at a temperature of 80° C.±5° C. under a pressure of from 10 to 100 mmHg, and then completely dissolved in 300 g of water.

The total amount of the reaction mixture was then allowed to pass through a column filled with 100 g of a strongly acidic cation exchange resin [Diaion SKN-1, produced by Mitsubishi Chemical Corporation]. The effluent from the column was then put into a separatory funnel. To the effluent was then added 30 g of sodium chloride. The mixture was then stirred until it completely dissolved. To the solution was then added 300 g of dichloromethane. The mixture was vigorously shaken, and then allowed to stand for 20 minutes. The resulting dichloromethane phase was then separated as a lower phase. The dichloromethane phase thus obtained was taken in a 1 l ground-glass eggplant type flask with a rotary evaporator where it was then concentrated to dryness at a temperature of 40° C.±5° C. Subsequently, 200 g of chloroform were put in the eggplant type flask. The reaction mixture was then stirred at a temperature of 50° C.±5° C. for 30 minutes so that the majority of solid matters was dissolved. Sodium chloride thus deposited as an insoluble content was withdrawn by filtration, and then concentrated to dryness by the rotary evaporator to obtain 46.8 g of a methoxypolyoxiranemonosuccinic acid ester.

Figure 14:
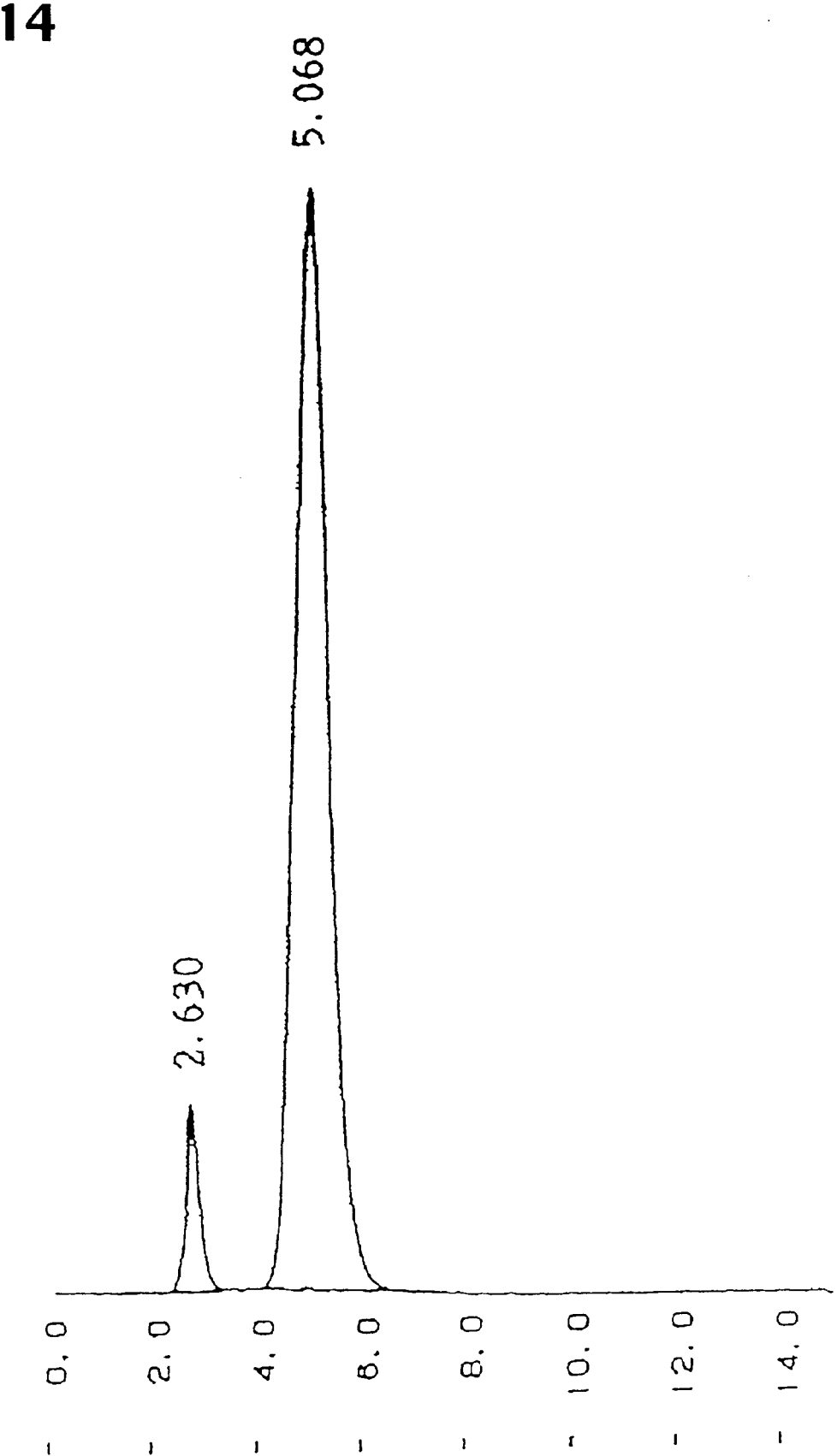
FIG. 14 illustrates the liquid chromatogram of a methoxypolyoxiranemonosuccinic acid ester of Example 6.

The methoxypolyoxiranemonosuccinic acid ester thus obtained was then subjected to analysis by liquid chromatography. For liquid chromatography, Shimadzu LC-10A was used as a chromatograph. A differential refratometer (x 0.25) was used as a detector. A 5 mM ammonium formate buffer (pH 8.0) was used as an eluent. ASAHIPAK ES-502N (I.D. 7.5 mm×100 mm) was used as a column. The liquid chromatography was then effected at a flow rate of 1 ml/min and a column temperature of 30° C. The sample size was 1%×20 µl. The liquid chromatogram thus obtained is shown in FIG. 14. The chromatogram showed that the methoxypolyoxiranemonosuccinic acid ester thus obtained comprises only a methoxypolyoxiranemonosuccinic acid ester as a main component and unreacted methoxypolyoxirane. The purity of the main component determined by liquid chromatography was 94.2% by weight.

Comparative Example 5

A methoxypolyoxiranemonosuccinic acid ester was synthesized in the same manner as in Example 6 except that the methoxypolyoxirane prepared in Example 2 was replaced by the commercially available methoxypolyoxirane analyzed in Comparative Example 3 (reagent produced by Aldrich Corp.; Mw=5,000).

Figure 15:
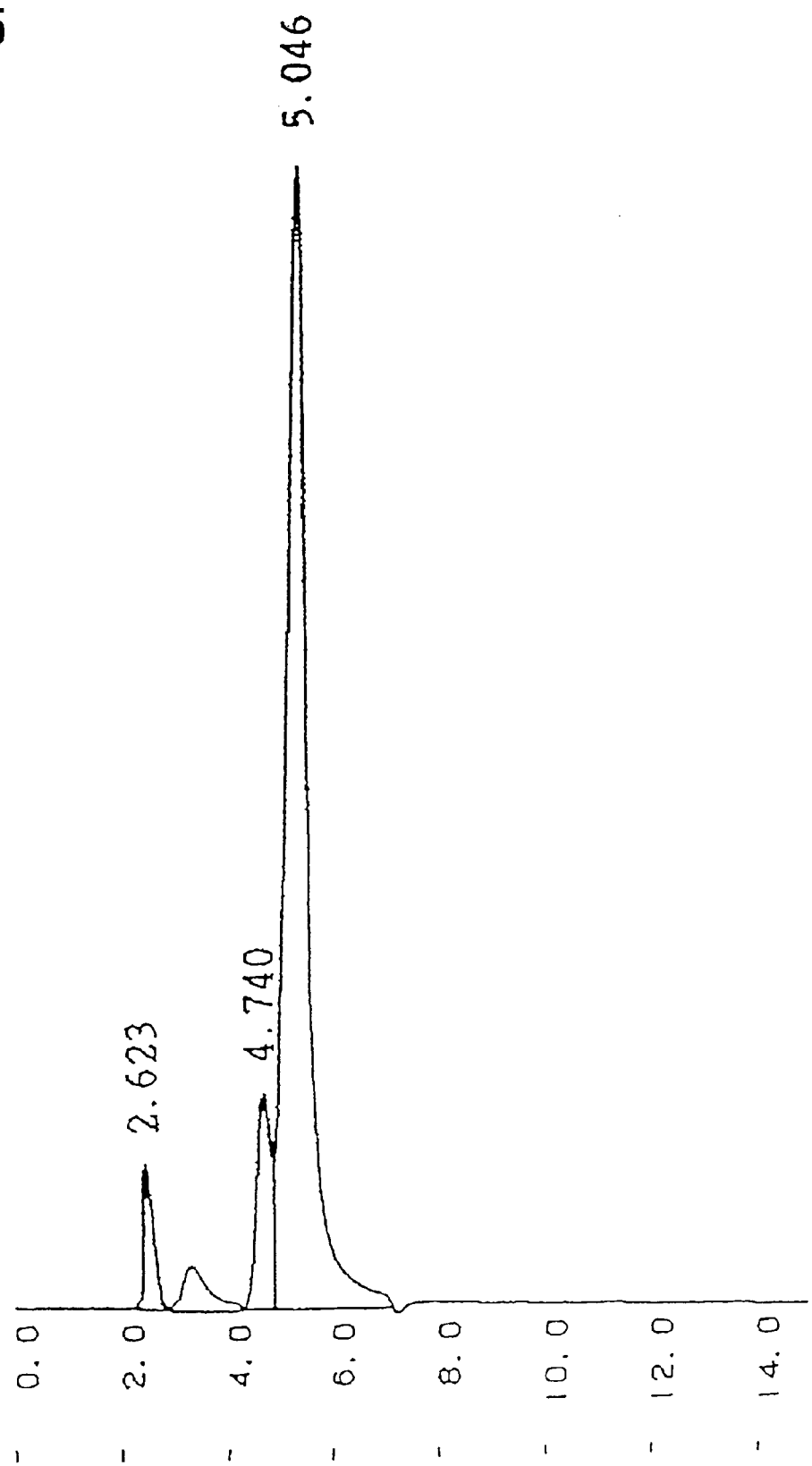
FIG. 15 illustrates the liquid chromatogram of a methoxypolyoxiranemonosuccinic acid ester of Comparative Example 5.

The methoxypolyoxiranemonosuccinic acid ester thus obtained was then subjected to analysis by liquid chromatography in the same manner as in Example 6. The liquid chromatogram thus obtained is shown in FIG. 15. The chromatogram showed that the methoxypolyoxiranemonosuccinic acid ester thus obtained comprises various impurities besides a methoxypolyoxiranemonosuccinic acid ester as a main component and unreacted methoxypolyoxirane.

The purity of the main component determined by liquid chromatography was 83.6% by weight.

The results of Example 6 and Comparative Example 5 showed that the use of a methoxypolyoxirane obtained by the process of the present invention makes it easy to obtain a high purity derivative.

Example 7

5.9 g (0.001 mol) of the methoxypolyoxiranemonosuccinic acid ester prepared in Example 6 and 100 ml of chloroform were put in a 300 ml ground stopper eggplant type flask. The mixture was then stirred until it completely dissolved. Subsequently, to the solution was added 516 mg (0.00095 mol) of adriamycin [reagent produced by Merck Japan Ltd.; Model No. 100788] as a hydrophobic chemical having amino group. The mixture was then stirred until it became homogeneous. Subsequently, to the mixture was added 206.3 mg (0.001 mol) of dicyclohexylcarbodimide [DCC, produced by Kanto Chemical Co., Ltd.; reagent class, Model No. 10190-00] as a dehydrating agent. The mixture was then stirred at a temperature of 50° C.±5° C. for 3 hours. To the mixture was then added 200 μl of ion-exchanged water. The mixture was then stirred at a temperature of 50° C.±5° C. for 1 hour. Dicyclohexylurea (DCU) thus precipitated was then removed by filtration. The resulting filtrate was then concentrated to dryness by means of an evaporator. To the solid matter thus obtained was then added 10 g of chloroform to make complete dissolution. To the solution was then gradually added 100 g of hexane with stirring to cause crystallization. The solution which had thus undergone crystallization was then stirred at room temperature for 3 hours. The crystal thus formed was then withdrawn by filtration. The crystal thus obtained was then dried at room temperature under reduced pressure (10 to 50 mmHg) for 12 hours to remove residual solvent therefrom. The crystal thus obtained exhibited an acid value of 0.0. The yield of the product was 5.6 g.

1 g of the crystal thus obtained was then taken in a screw pipe. To the crystal was then added 20 g of ion-exchanged water. The mixture was stirred at a temperature of 40° C. for 30 minutes, and then measured for transmission at a wavelength of 650 nm. The results were 99.5%.

Comparative Example 6

The reaction with adriamycin and purification were effected in the same manner as in Example 7 except that the methoxypolyoxiranemonosuccinic acid ester prepared in Example 6 was replaced by the methoxypolyoxiranemonosuccinic acid ester prepared in Comparative Example 5.

The crystal thus obtained was then measured for transmission at a wavelength of 650 nm in the same manner as in Example 7. The results were 72.8%. Further, the resulting aqueous solution looked cloudy. This is probably because 1 mol of polyoxiranedisuccinic acid ester as an impurity contained in the methoxypolyoxiranemonosuccinic acid ester and 2 mol of adriamycin react with each other to produce a chemical that makes it impossible for polyoxirane to sufficiently relax the hydrophobicity of adriamycin.

Example 8

It was tried to synthesize a compound represented by the general formula [2] in accordance with the process disclosed in JP-A-8-165343.

A 2 l four-neck flask was then equipped with a reflux condenser, a nitrogen gas blowing tube, a thermometer, an agitator and a dropping funnel. Into the four-neck flask were then put 254.6 g (0.02 mol) of the methoxy polyoxirane (PtopMw=12.730) prepared in Example 3, 1,000 g of acetonitrile and 1.5 g of a 10 wt-% aqueous solution of NaOH. The mixture was then stirred at a temperature of 30° C.±2° C. with nitrogen gas being blown thereinto until the methoxy polyoxirane was completely dissolved. Subsequently, 4.5 g of acrylonitrile and 40 g of acetonitrile were put in a dropping funnel from which the mixture was then added dropwise to the reaction solution at a temperature of 30° C.±2° C. in 2 hours. After the end of dropwise addition, the reaction mixture was ripened at the same temperature for 2 hours. To the reaction mixture thus ripened was then added 10 g of an alkali adsorbent [KYOWORD KW#700, produced by KYOWA CHEMICAL INDUSTRIES, LTD.]. The reaction mixture was stirred at the same temperature for 30 minutes, and then filtered under pressure to remove the catalyst therefrom. Subsequently, the total amount of the filtrate thus obtained was put in a 2 l ground-glass eggplant type flask equipped with a rotary evaporator where it was then distilled at a temperature of 80° C.±10° C. under a pressure of not higher than 30 mmHg so that unreacted acrylonitrile and acetonitrile as solvent were removed away to obtain 243 g of a cyanoethylated methoxy poyoxirane.

Subsequently, 200 g of the cyanoethylated methoxy polyoxirane, 200 g of toluene and 12 g of Ni-5316P (produced by ENGELHARD DE MEERN B. V.) as a Raney-nickel catalyst were put in an autoclave for hydrogen reduction. The interior of the autoclave was then compressed at a pressure of 7 kg/cm$^2$ with stirring while being kept at a temperature of 60° C. Subsequently, hydrogen gas was gradually pressed into the autoclave while the temperature of the autoclave was being controlled to 130° C.±5° C. The reaction mixture was then allowed to undergo reaction while the inner pressure of the autoclave was being kept at 35±5kg/cm$^2$ for 5 hours. The reaction system was then allowed to cool to 70° C.±5° C. The gas in the autoclave was discharged so that the pressure in the autoclave was turned to the ordinary pressure. The reaction product was then filtered under pressure to remove the catalyst. Subsequently, the total amount of the filtrate thus obtained was taken in a 1 l eggplant type flask equipped with a rotary evaporator where it was then distilled at a temperature of 80° C.±10° C. under a pressure of not higher than 30 mmHg so that ammonia and toluene were removed away to obtain 184 g of crude methoxypolyoxirane monoamine.

Subsequently, a column was filled with 100 g of a base-exchange type ion-exchange resin regenerated by ordinary method [DIAION PK-216, produced by Mitsubishi Chemical Corporation]. 10 g of the crude methoxypolyoxirane monoamine thus obtained was dissolved in 90 g of ion-exchanged water, and then allowed to flow through the column filled with ion-exchanged water at a rate of 0.8 ml/min. When the level of the liquid in the column was flush with the border of the resin, 1 l of ion-exchanged water was then allowed to flow at a rate of 3.3 ml/min. Subsequently, 0.5 l of a 5 wt-% aqueous ammonia was allowed to flow at a rate of 0.8 ml/min. Subsequently, the effluent thus collected was freeze-dried to obtain 7.5 g of the desired methoxypolyoxirane monoamine.

The methoxypolyoxirane monoamine thus obtained exhibited a total amine value of 4.30, a primary amine value of 4.30, a secondary amine value of 0 and a tertiary amine value of 0. The purity of methoxypolyoxirane monoamine calculated from amine value was 98.0%.

Figure 16:
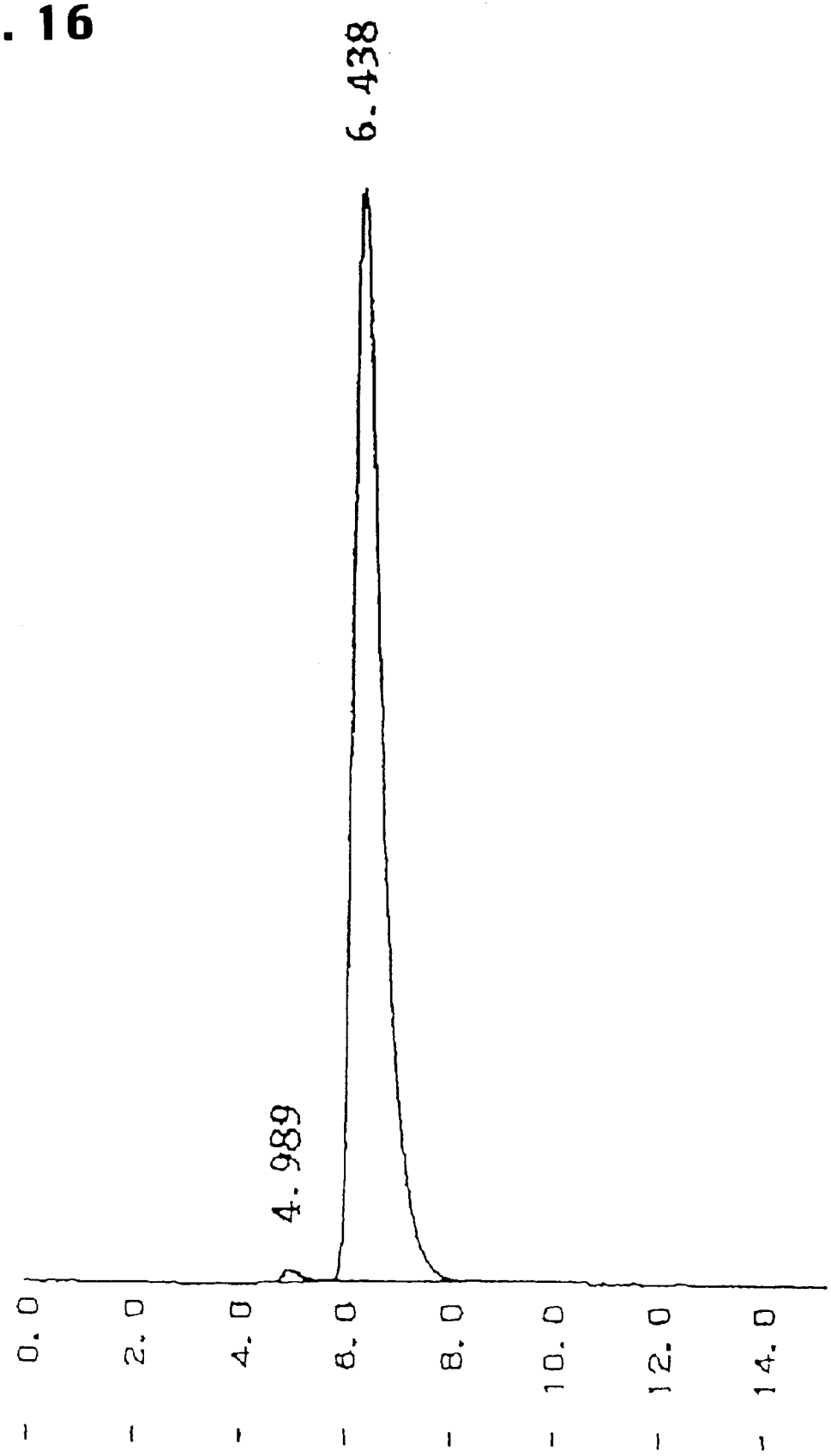
FIG. 16 illustrates the liquid chromatogram of a methoxypolyoxiranemonoamine of Example 8.

The methoxypolyoxirane monoamine thus obtained was then subjected to analysis by liquid chromatography. For liquid chromatography, TSKgel SP-5PW (produced by TOSOH CORP.) was used as a column. A 2 mM phosphoric acid buffer (pH 7.4) was used as a developing solvent. The liquid chromatography was then effected at a column oven temperature of 30° C. and a flow rate of 0.5 ml/min. The sample concentration was 0.5 (w/v) %. The injected amount of the sample was 20 μl. The liquid chromatogram thus obtained is shown in FIG. 16. The liquid chromatogram showed that the methoxypolyoxirane monoamine thus obtained comprises only a methoxypolyoxirane as a main component and a slight amount of unreacted methoxypolyoxirane.

Example 9

A methoxypolyoxirane monoamine was prepared in the same manner as in Example 8 except that the methoxyoxirane (PtopMw=12,730) prepared in Example 3 was replaced by the methoxyoxirane (PtopMw=5,800) prepared in Example 2.

The methoxypolyoxirane monoamine thus obtained exhibited a total amine value of 9.48, a primary amine value of 9.48, a secondary amine value of 0 and a tertiary amine value of 0. The purity of methoxypolyoxirane monoamine calculated from amine value was 98.0%.

Subsequently, it was tried to synthesize an oxirane derivative for drug delivery in accordance with the process disclosed in JP-A-2-300133.

4.98 g (0.02 mol) of β-benzyl-L-aspartate-N-carboxylic acid (BLA-NCA) was dissolved in 12 ml of N,N'-dimethylformamide. To the solution was then added 60 ml of chloroform. Subsequently, 5.8 g (0.001 mol) of the methoxypolyoxirane monoamine previously obtained was dissolved in 60 ml of chloroform. The solution thus obtained was then added to BLA-NCA solution. The mixture was then stirred at room temperature by means of a magnetic stirrer for 70 hours. The reaction solution was then added dropwise to 2,000 ml of diethyl ether. The resulting crystal was withdrawn by filtration, washed with 500 ml of diethyl ether, and then dried under reduced pressure to obtain a monomethoxypolyoxirane-poly(β-benzyl-L-aspartate) block copolymer (MePEG-PBLA). The yield of the product was 9.38 g (87.0%).

Subsequently, 100 mg of MePEG-PBLA thus obtained was dissolved in 5 ml of dichloromethane. The solution thus obtained was then added dropwise to 50 ml of syringe water with stirring. The mixture was then stirred at room temperature for 1 hour. The total amount of the mixture was put in an evaporator where dichloromethane was then distilled off under a pressure of 300 mmHg. The micell solution thus obtained was then measured for average micelle diameter by means of a light-scattering particle size distribution meter. The results were 82 nm.

Comparative Example 7

A methoxypolyoxiranemonoamine and MePEG-PBLA were synthesized from the methoxyoxirane (reagent (Mw= 5,000; PtopMw=5,638) produced by Aldrich Corp.) analyzed in Comparative Example 3 in the same manner as in Example 9.

The methoxypolyoxiranemonoamine thus obtained exhibited a total amine value of 9.70, a primary amine value of 9.70, a secondary amine value of 0 and a tertiary amine value of 0, and a purity of 97.5%.

Subsequently, MePEG-PBLA was synthesized from 5.63 g (0.001 mol) of a methoxypolyoxirane and 4.98 g (0.02 mol) of BLA-NCA in the same manner as in Example 9.

The yield of MePEG-PBLA thus obtained was 9.3 g (87.6%).

A micell solution was then prepared from MePEG-PBLA thus obtained in the same manner as in Example 9 to determine the average micelle diameter thereof. The results were 387 nm.

Comparative Example 8

A polyethylene glycol diamine was synthesized from PEG#11000 (polyethylene glycol (Mw=11,000) produced by NOF Corp.) in the same manner as in Example 8.

The polyethylene glycol thus obtained exhibited a total amine value of 9.91, a primary amine value of 9.91, a secondary amine value of 0, a tertiary amine value of 0, and a purity of 97.1%.

Subsequently, a polyethylene glycol-di-poly(β-benzyl-L-aspartate) block copolymer (PEG-Di-PBLA) was synthesized from 5.50 g (0.0005 mol) of a polyethylene glycol diamine and 4.98 g (0.02 mol) of BLA-NCA in the same manner as in Example 9.

The yield of PEG-Di-PBLA thus obtained was 8.76 g (85.8%).

Subsequently, 5 mg of PEG-Di-PBLA and 95 mg of MePEG-PBLA were dissolved in 5 ml of dichloromethane. The solution thus obtained was then added dropwise to 50 ml of syringe water. The mixture was then stirred at room temperature for 1 hour. The total amount of the mixture was put in an evaporator where dichloromethane was then distilled off under a pressure of not higher than 300 mmHg. The micelle solution thus obtained was then measured for average micelle diameter by means of a light-scattering particle size distribution meter (NICOMP model 370, produced by NICOMP CORP.). The results were 338 nm.

The comparison of Example 9 with Comparative Examples 7 and 8 shows that the product of Example 9 has a micelle particle diameter as small as 82 nm while the product of Comparative Example 7, which comprises a methoxyoxirane containing a high molecular by-product, and the product of Comparative Example 8, which comprises the product of Example 9 having a polyethylene glycol diamine derived from PEG#11000, which is a compound having a both end hydroxyl value as much as about twice the molecular weight of methoxyoxirane, added thereto, have a micelle particle diameter of 387 nm and 338 nm, respectively.

If the micelle diameter increases as mentioned above, micelle is agglomerated and sedimented with time in drug delivery system to disadvantage. Further, if the micelle has a great diameter, it can be easily caught by RES cells such as those of the kidney and spleen in the human body to possibly aggravate its retention in the blood, restricting the use of drug delivery system.

Industrial Applicability

The oxirane derivative of the present invention is a high purity and high molecular monoalkoxypolyoxirane having little content of low molecular and high molecular by-products and other impurities and hence a uniform distribution of molecular weight and polarity and thus can be used as a starting material of terminal-modified oxirane compound from which various drug delivery systems which have recently been noted in the art are prepared. The preparation process of the present invention makes it easy to obtain a high purity and high molecular terminal-modified oxirane compound. Further, terminal-modified oxirane compounds prepared from the oxirane derivative of the present invention as a starting material have a uniform molecular weight distribution and are free of impurities and thus allow accurate design and evaluation of drug.

What is claimed is:

1. An oxirane derivative represented by the following general formula (1):

$$RO(C_2H_4O)nH \qquad (1)$$

wherein R represents a $C_{1-7}$ hydrocarbon group; and n represents the average number of moles of oxirane groups added, ranging from 20 to 900, wherein the following requirements are satisfied:

(A) supposing that the straight line between the elution starting point and the elution end point on a chromatogram obtained by gel permeation chromatography is PbaseL, the total peak area above PbaseL is Parea, the height of the top of the maximum peak of refractive index: Ptop, with respect to PbaseL is PtopH, and the peak area between the point at which the height of the elution curve from the elution starting point toward Ptop, with respect to PbaseL is 1/5 of PtopH and the point at which the height of the elution curve from Ptop toward the elution end point, with respect to PbaseL is 1/5 of PtopH is PareaM, Parea and PareaM satisfy the following relationship:

$$PareaM/Parea > 0.85$$

and (B) when thin layer chromatography is effected by development with a 85:15 (by volume) mixture of chloroform and methanol, followed by color development with iodine and measurement of the purity of various spots by a densitometer, main spots having Rf values falling within the range of from 0.2 to 0.8 have a purity of not less than 98%.

2. The oxirane derivative according to claim 1, wherein Parea and PareaH satisfy the following relationship:

$$PareaH/Parea \leq 0.05$$

where PareaH is the peak area between the elution starting point on a chromatogram and the point at which the height of the elution curve toward Ptop from PbaseL is 1/5 of PtopH.

3. The oxirane derivative according to claim 1 or 2, wherein the number of moles of oxirane added PtopEOmol determined by the following equation:

$$PtopEOmol = (PtopMw - ROHMw)/44$$

supposing that the molecular weight corresponding to the top of the peak on a chromatogram is PtopMw and the molecular weight of the compound ROH (in which R represents a $C_{1-7}$ hydrocarbon atom) to be used as a starting material is ROHMw, satisfies the following relationship with the ratio PMmw/mn of weight-average molecular weight to number-average molecular weight of the region represented by PareaM determined by gel permeation chromatography:

$$PMmw/mn - [1 + PtopEOmol/(1 + PtopEOmol)^2] \leq 0.02.$$

4. The oxirane derivative according to claim 1 or claim 2, wherein R in the general formula (1) is $CH_3$.

5. A process for the preparation of an oxirane derivative as in claim 1 or claim 2, which comprises reacting the compound ROH (in which R represents a $C_{1-7}$ hydrocarbon group) with oxirane at a temperature of 50 to 130° C. and in a reaction system containing not more than 5 ppm water.

6. The process for the preparation of an oxirane derivative according to claim 5, wherein R in the general formula (1) is $CH_3$.

7. The oxirane derivative according to claim 3, wherein R in the general formula (1) is $CH_3$.

8. A process for the preparation of an oxirane derivative as defined in claim 3, which comprises reacting the compound ROH (in which R represents a $C_{1-7}$ hydrocarbon group) with oxirane at a temperature of 50 to 130° C. and in a reaction system containing not more than 5 ppm water.

9. The process for the preparation of an oxirane derivative according to claim 8, wherein R in the general formula (1) is $CH_3$.

10. The oxirane derivative according to claim 2, wherein PareaH/Parea is not more than 0.04.

11. The process for the preparation of an oxirane derivative according to claim 5, which comprises reacting the compound ROH (in which R represents a $C_{1-7}$ hydrocarbon group) with oxirane in the presence of a catalyst selected from the group consisting of metallic sodium, metallic potassium and an alkoxide of compound ROH.

12. The process for the preparation of an oxirane derivative according to claim 6, which comprises reacting the compound ROH (in which R represents $CH_3$) with oxirane in the presence of a catalyst selected from the group consisting of metallic sodium, metallic potassium and an alkoxide of compound ROH.

13. The process for the preparation of an oxirane derivative according to claim 8, which comprises reacting the compound ROH (in which R represents a $C_{1-7}$ hydrocarbon group) with oxirane in the presence of a catalyst selected from the group consisting of metallic sodium, metallic potassium and an alkoxide of compound ROH.

14. The process for the preparation of an oxirane derivative according to claim 9, which comprises reacting the compound ROH (in which R represents $CH_3$) with oxirane in the presence of a catalyst selected from the group consisting of metallic sodium, metallic potassium and an alkoxide of compound ROH.

15. The oxirane derivative according to claim 1, wherein PareaM/Parea is not less than 0.88.

16. The oxirane derivative according to claim 1, having a thin layer chromatography purity of not less than 99%.

17. The oxirane derivative according to claim 1, wherein n is from 50 to 900.

18. The oxirane derivative according to claim 1, wherein n is from 100 to 900.

19. The oxirane derivative according to claim 1, wherein R in general formula (1) is a $C_7$ hydrocarbon group.

20. The oxirane derivative according to claim 1, wherein R represents a $C_{1-4}$ hydrocarbon group.

21. The oxirane derivative according to claim 1, wherein R represents a $C_{1-2}$ hydrocarbon group.

22. An oxirane derivative represented by the following general formula (2) prepared by aminating or carboxylating an oxirane derivative of formula (1):

$$RO(C_2H_4O)_n—H \qquad (1)$$

$$RO(C_2H_4O)_n—Xp—Y \qquad (2)$$

wherein R represents a $C_{1-7}$ hydrocarbon group; n represents an integer of from 20 to 900; X represents a $C_{1-3}$ hydrocarbon group or —$CO(CH_2)q$— (in which q is an integer of from 2 to 4); Y represents an amino group or carboxyl group; and p represents 0 or 1, wherein said oxirane derivative of formula (1) satisfies the following requirements when subjected to gel permeation chromatography and thin layer chromatography:

(A) Supposing that the straight line between the elution starting point and the elution end point on chromatogram obtained by gel permeation chromatography is PbaseL, the total peak area above PbaseL is Parea, the height of the top of the maximum peak of refractive index: Ptop, with respect to PbaseL is PtopH, and the peak area between the point at which the height of the elution curve from the elution starting point toward Ptop, with respect to PbaseL is ⅕ of PtopH and the point at which the height of the elution curve from Ptop toward the elution end point, with respect to PbaseL is ⅕ of PtopH is PareaM, Parea and PareaM satisfy the following relationship:

$$PareaM/Parea \geq 0.85;$$

and (B) When thin layer chromatography is effected by development with a 85:15 (by volume) mixture of chloroform and methanol, followed by color development with iodine and measurement of the purity of various spots by a densitometer, main spots having Rf value falling within the range of from 0.2 to 0.8 have a purity of not less than 98%.

23. The oxirane derivative according to claim 22, wherein Parea and PareaH satisfy the following relationship:

$$PareaH/Parea \leq 0.05$$

where PareaH is the peak area between the elution starting point on a chromatogram and the point at which the height of the elution curve toward Ptop from PbaseL is ⅕ of PtopH.

24. The oxirane derivative according to claim 22, wherein R is $CH_3$.

25. The oxirane derivative according to claim 22, wherein Parea and PareaH satisfy the following relationship:

$$PareaH/Parea \leq 0.05$$

where PareaH is the peak area between the elution starting point on a chromatogram, and the point at which the height of the elution curve toward Ptop from PbaseL is ⅕ of PtopH and the number of moles of oxirane added PtopEOmol determined by the following equation:

$$PtopEOmol=(PtopMw-ROHMw)/44$$

supposing that the molecular weight corresponding to the top of a peak on a chromatogram is PtopMw and the molecular weight of the compound ROH (in which R represents a $C_{1-7}$ hydrocarbon group) to be used as a starting material is ROHMw, satisfies the following relationship with the ratio PMmw/mn of weight-average molecular weight to number-average molecular weight of the region represented by PareaM determined by gel permeation chromatography:

$$PMmw/mn-[1+PtopEOmol/(1+PtopEOmol)^2] \leq 0.02.$$

26. The oxirane derivative according to claim 22, wherein R is $CH_3$, Parea and PareaH satisfy the following relationship:

$$PareaH/Parea \leq 0.05$$

where PareaH is the peak area between the elution starting point on a chromatogram, and the point at which the height of the elution curve toward Ptop from PbaseL is ⅕ of PtopH and the number of moles of oxirane added PtopEOmol determined by the following equation:

$$PtopEOmol=(PtopMw-ROHMw)/44$$

supposing that the molecular weight corresponding to the top of a peak on a chromatogram is PtopMw and the molecular weight of the compound ROH (in which R represents $CH_3$) to be used as a starting material is ROHMw, satisfies the following relationship with the ratio PMmw/mn of weight-average molecular weight to number-average molecular weight of the region represented by PareaM determined by gel permeation chromatography:

$$PMmw/mn-[1+PtopEOmol/(1+PtopEOmol)^2] \leq 0.02.$$

27. The oxirane derivative according to claim 22, wherein n is from 50 to 900.

28. The oxirane derivative according to claim 22, wherein n is from 100 to 900.

29. The oxirane derivative according to claim 22, wherein R is a $C_7$ hydrocarbon group.

30. An oxirane derivative represented by the following general formula (2) prepared by aminating or carboxylating an oxirane derivative of formula (1):

$$RO(C_2H_4O)_n\text{—}H \tag{1}$$

$$RO(C_2H_4O)n\text{—}Xp\text{—}Y \tag{2}$$

wherein R represents a $C_{1-7}$ hydrocarbon group; n represents an integer of from 20 to 900; X represents a $C_{1-3}$ hydrocarbon group or —$CO(CH_2)q$— (in which q is an integer of from 2 to 4); Y represents an amino group or carboxyl group; and p represents 0 or 1, wherein said oxirane derivative of formula (1) satisfies the following requirements when subjected to gel permeation chromatography and thin layer chromatography:

(A) Supposing that the straight line between the elution starting point and the elution end point on chromatogram obtained by gel permeation chromatography is PbaseL, the total peak area above PbaseL is Parea, the height of the top of the maximum peak of refractive index: Ptop, with respect to PbaseL is PtopH, and the peak area between the point at which the height of the elution curve from the elution starting point toward Ptop, with respect to PbaseL is ⅕ of PtopH and the point at which the height of the elution curve from Ptop toward the elution end point, with respect to PbaseL is ⅕ of PtopH is PareaM, Parea and PareaM satisfy the following relationship:

$$PareaM/Parea \geq 0.85;$$

and (B) When thin layer chromatography is effected by development with a 85:15 (by volume) mixture of chloroform and methanol, followed by color development with iodine and measurement of the purity of various spots by a densitometer, main spots having Rf value falling within the range of from 0.2 to 0.8 have a purity of not less than 98%, wherein the number of moles of oxirane added PtopEOmol determined by the following equation:

$$PtopEOmol=(PtopMw-ROHMw)/44$$

supposing that the molecular weight corresponding to the top of a peak on a chromatogram is PtopMw and the molecular weight of the compound ROH (in which R represents a $C_{1-7}$ hydrocarbon atom) to be used as a starting material is ROHMw, satisfies the following relationship with the ratio PMmw/mn of weight-average molecular weight to number-average molecular weight of the region represented by PareaM determined by gel permeation chromatography:

$$PMmw/mn-[1+PtopEOmol/(1+PtopEOmol)^2] \leq 0.02.$$

31. An oxirane derivative represented by the following general formula (2) prepared by aminating or carboxylating an oxirane derivative of formula (1):

$$RO(C_2H_4O)_n—H \quad (1)$$

$$RO(C_2H_4O)n—Xp—Y \quad (2)$$

wherein R represents $CH_3$; n represents an integer of from 20 to 900; X represents a $C_{1-3}$ hydrocarbon group or $—CO(CH_2)q—$ (in which q is an integer of from 2 to 4); Y represents an amino group or carboxyl group; and p represents 0 or 1, wherein said oxirane derivative of formula (1) satisfies the following requirements when subjected to gel permeation chromatography and thin layer chromatography:

(A) Supposing that the straight line between the elution starting point and the elution end point on chromatogram obtained by gel permeation chromatography is PbaseL, the total peak area above PbaseL is Parea, the height of the top of the maximum peak of refractive index: Ptop, with respect to PbaseL is PtopH, and the peak area between the point at which the height of the elution curve from the elution starting point toward Ptop, with respect to PbaseL is ⅕ of PtopH and the point at which the height of the elution curve from Ptop toward the elution end point, with respect to PbaseL is ⅕ of PtopH is PareaM, Parea and PareaM satisfy the following relationship:

$$PareaM/Parea \geq 0.85;$$

and (B) When thin layer chromatography is effected by development with a 85:15 (by volume) mixture of chloroform and methanol, followed by color development with iodine and measurement of the purity of various spots by a densitometer, main spots having Rf value falling within the range of from 0.2 to 0.8 have a purity of not less than 98%, wherein the number of moles of oxirane added PtopEOmol determined by the following equation:

$$PtopEOmol=(PtopMw-ROHMw)/44$$

supposing that the molecular weight corresponding to the top of a peak on a chromatogram is PtopMw and the molecular weight of the compound ROH (in which R represents a $CH_3$) to be used as a starting material is ROHMw, satisfies the following relationship with the ratio PMmw/mn of weight-average molecular weight to number-average molecular weight of the region represented by PareaM determined by gel permeation chromatography:

$$PMmw/mn-[1+PtopEOmol/(1+PtopEOmol)^2] \leq 0.02.$$

32. A process for the preparation of an oxirane derivative represented by formula (2), which comprises aminating or carboxylating an oxirane derivative of formula (1):

$$RO(C_2H_4O)_n—H \quad (1)$$

$$RO(C_2H_4O)_n—Xp—Y \quad (2)$$

wherein R represents a $C_{1-7}$ hydrocarbon group; n represents an integer of from 20 to 900; X represents a $C_{1-3}$ hydrocarbon group or $—CO(CH_2)q—$ (in which q is an integer of from 2 to 4); Y represents an amino group or carboxyl group; and p represents 0 or 1, wherein said oxirane derivative of formula (1) satisfies the following requirements when subjected to gel permeation chromatography and thin layer chromatography:

(A) Supposing that the straight line between the elution starting point and the elution end point on chromatogram obtained by gel permeation chromatography is PbaseL, the total peak area above PbaseL is Parea, the height of the top of the maximum peak of refractive index: Ptop, with respect to PbaseL is PtopH, and the peak area between the point at which the height of the elution curve from the elution starting point toward Ptop, with respect to PbaseL is ⅕ of PtopH and the point at which the height of the elution curve from Ptop toward the elution end point, with respect to PbaseL is ⅕ of PtopH is PareaM, Parea and PareaM satisfy the following relationship:

$$PareaM/Parea \geq 0.85;$$

and (B) When thin layer chromatography is effected by development with a 85:15 (by volume) mixture of chloroform and methanol, followed by color development with iodine and measurement of the purity of various spots by a densitometer, main spots having Rf value falling within the range of from 0.2 to 0.8 have a purity of not less than 98%.

33. The process according to claim 32, wherein Parea and PareaH satisfy the following relationship:

$$PareaH/Parea \leq 0.05$$

where PareaH is the peak area between the elution starting point on a chromatogram and the point at which the height of the elution curve toward Ptop from PbaseL is ⅕ of PtopH.

34. The process according to claim 32, wherein R is $CH_3$.

35. The process according to claim 32, wherein Parea and PareaH satisfy the following relationship:

$$PareaH/Parea \leq 0.05$$

where PareaH is the peak area between the elution starting point on a chromatogram, and the point at which the height of the elution curve toward Ptop from PbaseL is ⅕ of PtopH and the number of moles of oxirane added PtopEOmol determined by the following equation:

$$PtopEOmol=(PtopMw-ROHMw)/44$$

supposing that the molecular weight corresponding to the top of a peak on a chromatogram is PtopMw and the molecular weight of the compound ROH (in which R represents a $C_{1-7}$ hydrocarbon group) to be used as a starting material is ROHMw, satisfies the following relationship with the ratio PMmw/mn of weight-average molecular weight to number-average molecular weight of the region represented by PareaM determined by gel permeation chromatography:

$$PMmw/mn-[1+PtopEOmol/(1+PtopEOmol)^2] \leq 0.02.$$

36. The process according to claim 32, wherein R is $CH_3$, and the point at which the height of the elution curve toward Ptop from PbaseL is ⅕ of PtopH and the number of moles of oxirane added PtopEOmol determined by the following equation:

$$PtopEOmol=(PtopMw-ROHMw)/44$$

supposing that the molecular weight corresponding to the top of a peak on a chromatogram is PtopMw and the molecular weight of the compound ROH (in which R represents $C_3$) to be used as a starting material is ROHNw, satisfies the following relationship with the ratio PMmw/mn of weight-average molecular weight to number-average molecular weight of the region represented by PareaM determined by gel permeation chromatography:

$$PMmw/mn-[1+PtopEOmol/(1+PtopEOmol)^2] \leq 0.02.$$

37. The process according to claim 32, wherein R is $CH_3$, Parea and PareaH satisfy the following relationship:

$$PareaH/Parea \leq 0.05$$

where PareaH is the peak area between the elution starting point on a chromatogram, and the point at which the height of the elution curve toward Ptop from PbaseL is 1/5 of PtopH and the number of moles of oxirane added PtopEOmol determined by the following equation:

$$PtopEOmol=(PtopMw-ROHMw)/44$$

supposing that the molecular weight corresponding to the top of a peak on a chromatogram is PtopMw and the molecular weight of the compound ROH (in which R represents $CH_3$) to be used as a starting material is ROHMw, satisfies the following relationship with the ratio PMmw/mn of weight-average molecular weight to number-average molecular weight of the region represented by PareaM determined by gel permeation chromatography:

$$PMmw/mn-[1+PtopEOmol/(1+PtopEOmol)^2] \leq 0.02.$$

38. The process according to claim 32, wherein n is from 50 to 900.

39. The process according to claim 32, wherein n is from 100 to 900.

40. The process according to claim 32, wherein R is a $C_7$ hydrocarbon group.

41. A process for the preparation of an oxirane derivative represented by formula (2), which comprises aminating or carboxylating an oxirane derivative of formula (1):

$$RO(C_2H_4O)_n\text{—}H \qquad (1)$$

$$RO(C_2H_4O)_n\text{—}Xp\text{—}Y \qquad (2)$$

wherein R represents a $C_{1-7}$ hydrocarbon group; n represents an integer of from 20 to 900; X represents a $C_{1-3}$ hydrocarbon group or —$CO(CH_2)q$— (in which q is an integer of from 2 to 4); Y represents an amino group or carboxyl group; and p represents 0 or 1, wherein said oxirane derivative of formula (1) satisfies the following requirements when subjected to gel permeation chromatography and thin layer chromatography:

(A) Supposing that the straight line between the elution starting point and the elution end point on chromatogram obtained by gel permeation chromatography is PbaseL, the total peak area above PbaseL is Parea, the height of the top of the maximum peak of refractive index: Ptop, with respect to PbaseL is PtopH, and the peak area between the point at which the height of the elution curve from the elution starting point toward Ptop, with respect to PbaseL is 1/5 of PtopH and the point at which the height of the elution curve from Ptop toward the elution end point, with respect to PbaseL is 1/5 of PtopH is PareaM, Parea and PareaM satisfy the following relationship:

$$PareaM/Parea \geq 0.85;$$

and (B) When thin layer chromatography is effected by development with a 85:15 (by volume) mixture of chloroform and methanol, followed by color development with iodine and measurement of the purity of various spots by a densitometer, main spots having Rf value falling within the range of from 0.2 to 0.8 have a purity of not less than 98%, wherein the number of moles of oxirane added PtopEOmol determined by the following equation:

$$PtopEOmol=(PtopMw-ROHMw)/44$$

supposing that the molecular weight corresponding to the top of a peak on a chromatogram is PtopMw and the molecular weight of the compound ROH (in which R represents a $C_{1-7}$ hydrocarbon atom) to be used as a starting material is ROHMw, satisfies the following relationship with the ratio PMmw/mn of weight-average molecular weight to number-average molecular weight of the region represented by PareaM determined by gel permeation chromatography:

$$PMmw/mn[1+PtopEOmol/(1+PtopEOmol)^2] \leq 0.02.$$

42. An oxirane derivative represented by the following general formula (1):

$$RO(C_2H_4O)_n\text{—}H \qquad (1)$$

wherein R represents a $C_{17}$ hydrocarbon group; and n represents an integer of from 50 to 900, said oxirane derivative of formula (1) is prepared by reacting ROH with oxirane at a temperature of from 50 to 130° C. in a reaction system having a water content of not more than 5 ppm, and wherein said oxirane derivative of formula (1) satisfies the following requirements when subjected to gel permeation chromatography and thin layer chromatography:

(A) Supposing that the straight line between the elution starting point and the elution end point on chromatogram obtained by gel permeation chromatography is PbaseL, the total peak area above PbaseL is Parea, the height of the top of the maximum peak of refractive index: Ptop, with respect to PbaseL is PtopH, and the peak area between the point at which the height of the elution curve from the elution starting point toward Ptop, with respect to PbaseL is 1/5 of PtopH and the point at which the height of the elution curve from Ptop toward the elution end point, with respect to PbaseL is 1/5 of PtopH is PareaM, Parea and PareaM satisfy the following relationship:

$$PareaM/Parea \geq 0.88;$$

and (B) When thin layer chromatography is effected by development with a 85:15 (by volume) mixture of chloroform and methanol, followed by color development with iodine and measurement of the purity of various spots by a densitometer, main spots having Rf value falling within the range of from 0.2 to 0.8 have a purity of not less than 98%.

* * * * *

(12) EX PARTE REEXAMINATION CERTIFICATE (9348th)
United States Patent
Yasukohchi et al.

(10) Number: US 6,455,639 C1
(45) Certificate Issued: Oct. 8, 2012

(54) OXIRANE DERIVATIVE AND PROCESS FOR THE PREPARATION THEREOF

(75) Inventors: Tohru Yasukohchi, Kanagawa (JP); Kouzoh Sanchika, Kanagawa (JP); Chika Itoh, Kanagawa (JP); Kei-ichi Maruyama, Kanagawa (JP)

(73) Assignee: NOF Corporation, Shibuya-Ku, Tokyo (JP)

Reexamination Request:
No. 90/009,911, Jun. 10, 2011

Reexamination Certificate for:
Patent No.: 6,455,639
Issued: Sep. 24, 2002
Appl. No.: 09/367,642
Filed: Aug. 19, 1999

(21) Appl. No.: 90/009,911

(22) PCT Filed: Mar. 23, 1999

(86) PCT No.: PCT/JP99/01451
§ 371 (c)(1),
(2), (4) Date: Aug. 19, 1999

(87) PCT Pub. No.: WO99/48948
PCT Pub. Date: Sep. 30, 1999

(30) Foreign Application Priority Data

Mar. 24, 1998 (JP) .................................. 10-076286

(51) Int. Cl.
*C08G 65/28* (2006.01)

(52) U.S. Cl. ........ 525/408; 525/409; 528/405; 528/421; 568/618; 568/621; 568/622

(58) Field of Classification Search ................. None
See application file for complete search history.

(56) References Cited

To view the complete listing of prior art documents cited during the proceeding for Reexamination Control Number 90/009,911, please refer to the USPTO's public Patent Application Information Retrieval (PAIR) system under the Display References tab.

*Primary Examiner* — Carlos Lopez

(57) ABSTRACT

An oxirane derivative and process for preparation of the same, having a high purity characterized in terms of gel permeation chromatography and thin layer chromatography. The oxirane derivative is useful as a starting material for medical purposes, and mainly drug delivery systems.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-4, 7, 10, 15-21 and 32-41 is confirmed.

Claims 11-14 and 22-31 are cancelled.

Claims 5, 8 and 42 are determined to be patentable as amended.

Claims 6 and 9, dependent on an amended claim, are determined to be patentable.

New claims 43-44 are added and determined to be patentable.

5. A process for the preparation of an oxirane derivative as in claim 1 or claim 2, which comprises reacting the compound ROH (in which R represents a $C_{1-7}$ hydrocarbon group) with oxirane *in the presence of a catalyst selected from the group consisting of metallic sodium, metallic potassium and an alkoxide of compound ROH* at a temperature of 50 to 130° C. and in a reaction system containing not more than 5 ppm water.

8. A process for the preparation of an oxirane derivative as defined in claim 3, which comprises reacting the compound ROH (in which R represents a $C_{1-7}$ hydrocarbon group) with oxirane *in the presence of a catalyst selected from the group consisting of metallic sodium, metallic potassium and an alkoxide of compound ROH* at a temperature of 50 to 130° C. and in a reaction system containing not more than 5 ppm water.

42. An oxirane derivative represented by the following general formula (1):

$$RO(C_2H_4O)_n\text{-}H \quad (1)$$

wherein R represents a [$C_{17}$] *$C_{1-7}$* hydrocarbon group; and n represents an integer of from 50 to 900, said oxirane derivative of formula (1) is prepared by reacting ROH with oxirane *in the presence of a catalyst selected from the group consisting of metallic sodium, metallic potassium and an alkoxide of compound ROH at a temperature of from 50 to 130° C. in a reaction system having a water content of not more than 5 ppm*, and wherein said oxirane derivative of formula (1) satisfies the following requirements when subjected to gel permeation chromatography and thin layer chromatography:

(A) Supposing that the straight line between the elution starting point and the elution end point on chromatogram obtained by gel permeation chromatography is PbaseL, the total peak area above PbaseL is Parea, the height of the top of the maximum peak of refractive index: Ptop, with respect to PbaseL is PtopH, and the peak area between the point at which the height of the elution curve from the elution starting point toward Ptop, with respect to PbaseL is ⅕ of PtopH and the point at which the height of the elution curve from Ptop toward the elution end point, with respect to PbaseL is ⅕ of PtopH is PareaM, Parea and PareaM satisfy the following relationship:

PareaM/Parea≧0.88;

and (B) When thin layer chromatography is effected by development with a 85:15 (by volume) mixture of chloroform and methanol, followed by color development with iodine and measurement of the purity of various spots by a densitometer, main spots having Rf value falling within the range of from 0.2 to 0.8 have a purity of not less than 98%.

*43. The oxirane derivative according to claim 1, wherein n is from 289 to 900.*

*44. The oxirane derivative according to claim 1, wherein n is from 473 to 900.*

\* \* \* \* \*